US 009951359B2

(12) United States Patent
Elkins et al.

(10) Patent No.: US 9,951,359 B2
(45) Date of Patent: Apr. 24, 2018

(54) HEAT-STABLE, FE-DEPENDENT ALCOHOL DEHYDROGENASE FOR ALDEHYDE DETOXIFICATION

(71) Applicant: UT-BATTELLE, LLC, Oak Ridge, TN (US)

(72) Inventors: James G. Elkins, Knoxville, TN (US); Sonya Clarkson, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 90 days.

(21) Appl. No.: 15/060,078

(22) Filed: Mar. 3, 2016

(65) Prior Publication Data

US 2016/0340702 A1   Nov. 24, 2016

Related U.S. Application Data

(62) Division of application No. 14/310,725, filed on Jun. 20, 2014, now abandoned.

(60) Provisional application No. 61/838,961, filed on Jun. 25, 2013.

(51) Int. Cl.
*C12P 7/06* (2006.01)
*C12P 17/04* (2006.01)
*C12N 9/04* (2006.01)
*C12P 7/10* (2006.01)

(52) U.S. Cl.
CPC ............ *C12P 17/04* (2013.01); *C12N 9/0006* (2013.01); *C12P 7/10* (2013.01); *C12Y 101/01002* (2013.01); *C12P 2201/00* (2013.01); *Y02E 50/16* (2013.01)

(58) Field of Classification Search
None
See application file for complete search history.

(56) References Cited

U.S. PATENT DOCUMENTS

| | | |
|---|---|---|
| 7,253,001 B2 | 8/2007 | Wahlbom et al. |
| 8,039,239 B2 | 10/2011 | Reeves |
| 8,110,387 B2 | 2/2012 | Hahnhagerdal et al. |
| 2007/0155000 A1 | 7/2007 | Nilsson et al. |
| 2011/0059485 A1 | 3/2011 | Calazza et al. |
| 2011/0177579 A1 | 7/2011 | Ma et al. |
| 2012/0108855 A1 | 5/2012 | Ingram et al. |
| 2012/0190089 A1 | 7/2012 | Buelter et al. |
| 2014/0120592 A1 | 5/2014 | Cha et al. |

OTHER PUBLICATIONS

He et al., Bioresource Technol. 102:9586-9592, 2011.*
Elkins et al., "Furan aldehyde detoxification by a heat-stable alcohol dehydrogenase from Thermoanaerobacter pseudethanolicus 39E", Abstract for the Symposium on Biotechnology for Fuels and Chemicals, Apr. 29, 2014, 1 page.*
Carere et al., BMC Microbiol. 12:295, 2012, 21 pages.*
Li, Q., et al., "Biochemical Characterization of ethanol-dependent reduction of furfural by alcohol dehydrogenases", (2011b) Biodegradation 22:1227-1237.
Wilson et al., J. Mol. Biol. 297:233-249, 2000.
Radianingtyas et al., FEMS Microbial. Rev. 27:593-616, 2003.
Clarkson et al., Biotechnol. Biofuels 7:165, 2014, 14 pages.
Gen Bank Accession No. CP000924, Jan. 2012, 2 pages.
Gen Bank Accession No. CP002466, Nov. 2011, 2 pages.
Alfani, F., et al., "Comparison of SHF and SSF processes for the bioconversion of steam-exploded wheat straw", (2000) J. Ind. Microbiol. Biotechnol., 25:184-192.
Almeida, J. RM., et al., "Mini-Review, Increased tolerance and conversion of inhibitors in lignocellulosic hydrolysates by *Saccharomyces cerevisiae*", (2007) J. Chem. Technol. Biotechnol. 82:340-349.
Argyros, D.A., et al., "High Ethanol Titers from Cellulose by Using Metabolically Engineered Thermophilic, Anaerobic Microbes", (Sep. 30, 2011) Appl, Environ. Microbiol., 77(23):8288-8294.
Bergquist, P.L., et al., "Molecular diversity of thermophilic cellulolytic and hemicellulolytic bacteria", (1999) FEMS Microbiol. Ecol., 28:99-110.
Blumer-Schuette, S.E., et al., "Extremely thermophilic microorganisms for biomass conversion: status and prospects", (2008) Curr. Opin. Biatechnol., 19:210-217.
Blumer-Schuette, et al.,"Phylogenetic, Microbiological, and Glycoside Hydrolase Diversities within the Extremely Thermophilic, Plant Biomass-Degrading Genus Caldicellulosiruptor", (2010) App. Microbiol.76(24):8084-8092.
Blumer-Schuette, S.E., et al.,"Complete Genome Sequences for the Anaerobic, Extremely Thermophilic Plant Biomass-Degrading Bacteria Caldicellulosiruptor hydrothermalis, Caldicellulosiruptor kristjanssonii, Caldicellulosiruptor cronotskyensis, Caldicellulosiruptor owensensis, and Caldicellulosiruptor lactoaceticus", (2011) J. Bacteriol. 193 (6)1483-1484; pub Mar. 2011; e-published Jan. 7, 2011.
Bowman, M.J., et al., "Stereochemistry of Furfural Reduction by a *Saccharomyces cerevisiae* Aldehyde Reductase That Contributes to In Situ Furfural Detoxification", (2010) Appl. Environ. Microbiol., 76(15):4926-4932.
Cha M. et al. "Metabolic engineering of Caldicellulosiruptor bescii yields increased hydrogen production from ignocellulosic biomass", (2013) Biotechnology for Biofuels, 6(85):1-8.

(Continued)

*Primary Examiner* — David Steadman
(74) *Attorney, Agent, or Firm* — Scully, Scott, Murphy & Presser, P.C.

(57) ABSTRACT

The present invention relates to microorganisms and polypeptides for detoxifying aldehydes associated with industrial fermentations. In particular, a heat-stable, NADPH- and iron-dependent alcohol dehydrogenase was cloned from *Thermoanaerobacter pseudethanolicus* 39E and displayed activity against a number of aldehydes including inhibitory compounds that are produced during the dilute-acid pretreatment process of lignocellulosic biomass before fermentation to biofuels. Methods to use the microorganisms and polypeptides of the invention for improved conversion of bio mass to biofuel are provided as well as use of the enzyme in metabolic engineering strategies for producing longer-chain alcohols from sugars using thermophilic, fermentative microorganisms.

12 Claims, 14 Drawing Sheets

(56) References Cited

OTHER PUBLICATIONS

Hung, D., et al., "Construction of a Stable Replicating Shuttle Vector for Caldicellulosiruptor Species: Use for Extending Genetic Methodologies to Other Members of This Genus", (May 2013) PLoS One 8(5): 1-10, e62881. doi:10.1371/journal.pone.0062881.
Chung, D., et al., "Direct conversion of plant biomass to ethanol by engineered Caldicellulosiruptor bescii", (Jun. 17, 2014) PNAS, 111(24):8931-8936.
Elkins, J.G., et al., "Engineered microbiol systems for enhanced conversion of lignocellulosic biomass", (2010) Curr. Opin. Biotechnol., 21:657-662.
Farkas J. et al., "Improved growth media and culture techniques for genetic analysis and assessment of biomass utilization by Caldicellulosiruptor bescii", (2013) J. Ind. Microbiol. Biatechnol., 40:41-49.
Hamilton-Brehm, S.D., et al., "*Caldicellulosiruptor obsidiansis* sp. nov., an Anaerobic, Extremely Thermophilic, cellulolytic Bacterium Isolated from Obsidian Pool, Yellowstone Park", (Dec. 18, 2010) App. Environ. Microbiol., 76(4):1014-1020.
Klinke, H.B., et al., "Inhibition of ethanol-producing yeast and bacteria by degradation products produced during pre-treatment of biomass", (2004) Appl. Microbiol. Biotechnol., 66:10-26.
Larroy, C., et al., "Characterization of the *Saccharomyces cerevisiae* YMR318C (ADH6) gene product as a broad specificity NADPH-dependent alcohol dehydrogenase: relevance in aldehyde reduction", (2002) Biochem. J., 361:163-172.
Larsson, S., et al., "Development of a *Saccharomyces cerevisiae* Strain with Enhanced Resistance to Phenolic Fermentation Inhibitors in Lignocellulose Hydrolysates by Heterologous Expression of Laccase", (2001) Appl. Environ. Microbiol., 67(3):1163-1170.
Li, Q. et al., "Cupriavidus necator JMP134 rapidly reduces furfural with a ZN-dependent alcohol dehydrogenase", (2011a) Biodegradation, 22:1215-1225.
Liu, Z.L., et al., "Adaptive response of yeasts to furfural and 5-hydroxymethylfurfural and new chemical evidence for HMF conversion to 2,5-bis-hydroxymethylfuran", (2004) J. Ind. Microbiol. Biotechnol., 31:345-352.
Liu, Z.L., et al., "Multiple gene-mediated NAD(P)H-dependent aldehyde reduction is a mechanism of in situ detoxification of furfural and 5-hydroxymethylfurfural *Saccharomyces cerevisiae* ", (2008) Appl. Microbiol. Biotechnol., 81:743-753.
Lovitt, R.W., et al., "Ethanol Production by Thermophilic Bacteria: Physiological Comparison of Solvent Effects on Parent and Alcohol-Tolerant Strains of Clostridium thermohydrosulfuricum", (1984) App. Microbiol., 48(1):171-177.
Lynd, L R. et al., "How biotech can transform biofuels", (Feb. 2008) Nat. Biotechnol., 26(2):169-172.
Lynd, L.R., et al., "Microbiol Cellulose Utilization: Fundamentals and Biotechnology", (2002) Microbiol. Mol. Biol. Rev., 66(3):506-577.
Mai, V., et al., "Transformation of *Thermoanaerobacterium* sp. strain JW/SL-Y5485 with plasmid pIKM1 conferring kanamycin resistance", (1997) FEMS Microbiol. Let, 148:163-167.
Mielenz, J.R., "Biofuels and Biotechnology", (2009) Molecular Biology and Biotechnology, 5th Edition, Ed. J.M. Walker & R. Rapley, Royal Society of Chemistry, pp. 548-584.
Mielenz, J.R., et al., "Cellulose and xylan fermentation by Caldicellulosiruptor obsidiansis", Abstract from "The 32nd Symposium on Biotechnology for Fuel and Chemicals" (Apr. 19-22, 2010).
Miller, T.L. and Wolin, M.J., "A Serum Bottle Modification of the Hungate Technique for Cultivating Obligate Anaerobes", (1974) Appl. Microbiol., 27(5):985-987.
Miller, E.N., et al., "Silencing of NADPH-Dependent Oxidoreductase Genes (yqhD and dkgA) in Furfural-Resistant Ethanologenic *Escherichia coli* ", (2009) Appl. Environ. Microbiol., 75(13):4315-4323.
Olson, D.G., et al., "Recent progress in consolidated bioprocessing", (2012) Curr. Opin. Biotechnol., 23:396-405.
Palmqvist, E., et al., "Fermentation of lignocellulosic hydrolysates. I: inhibition and detoxification", (2000a) Bioresource Technol., 74:17-24.
Palmqvist, E., et al., "Fermentation of lignocellulosic hydrolysates. II: inhibition and detoxification" (2000b) Bioresource Technol., 74:25-33.
Park, S., et al., "Expression of aldehyde dehydrogenase 6 reduces inhibitory effect of furan derivatives on cell growth and ethanol production in *Saccharomyces cerevisiae* ", (2011) Bioresource Biotechnol.102:6033-6038.
Petersson, A., et al., "A 5-hydroxymethyl furfural reducing enzyme encoded by the *Saccharomyces cerevisiae* ADH6 gene conveys HMF tolerance", (2006) Yeast, 23:455-464.
Raman, B., et al., "Impact of Pretreated Switchgrass and Biomass Carbohydrates on Clostridium thermocellum ATCC 27405 Cellulosome Composition: A Quantitative Proteomic Analysis", (Apr. 2009) PLoS One 4(4): 1-13, e5271.
Raman, B., et al., "Transcriptomic analysis of Clostridium thermocellum ATCC 27405 cellulose fermentation", (2011) BMC Microbiol.,11:134, pp. 1-15.
Shaw, A.J, et al., "Natural Competence in Thermoanaerobacter and Thermoanerobacterium Species", (2010) Appl. Environ. Microbiol., 76(14):4713-4719.
Spindler, D.D., et al., "Thermotolerant Yeast for Simultaneous Saccharification and Fermentation of Cellulose to Ethanol", (1988) Appl. Biochem. Biotechnol., 17:279-294.
Takagi, M., et al., "A Method for Production of Alcohol Directly from Cellulose Using Cellulase and Yeast", (1977) in Proceedings of the Bioconversion Symposium, Indian Institute of Technology, New Delhi, pp. 551-571.
Taylor, M.P., et al., "Understanding physiological responses to pre-treatment inhibitors in ethanologenic fermentations", (2012) Biotechnol. J., 7:1169-1181.
Tripathi, S.A., et al., "Development of pyrF-Based Genetic System for Targeted Gene Deletion in Clostridium thermocellum and Creation of a pta Mutant", (2010) Appl, Environ. Microbiol. 76(19):6591-6599.
Vanfossen, A.L., et al., "Polysaccharide Degradation and Synthesis by Extremely Thermophilic Anaerobes", (2008) Ann. N.Y. Acad. Sci., 1125:322-337.
Wang, X., et al., "Increased Furfural Tolerance Due to Overexpression of NADH-Dependent Oxidoreductase FucO in *Escherichia coli* Strains Engineered for the Production of Ethanol and Lactate", (2011) Appl. Environ. Microbiol., 77 (15):5132-5140.
Wang, X., et al., "Increased Furan Tolerance in *Escherichia coli* Due to a Cryptic ucpA Gene", (2012) Appl. Environ. Microbiol., 78(7):2452-2455.
Nystrom, J.M. and Allen, A.L., "Enzymatic Conversion of Cellulosic Materials: Technology and Applications, Pilot Scale Investigations and Economics of Cellulase Production", (1976) Biotechnol. & Bioeng. Symp. No. 6, pp. 55-74.
Wolin, E.A., et al., "Formation of Methane by Bacterial Extracts", (1963) J. Biol. Chem., 238:2882-2886.
Yang, S., et al., "The Zymomonas mobilis regulator hfq contributes to tolerance against multiple lignocellulosic pretreatment inhibitors", (2010) BmC Microbiol., 10:135, pp. 1-11.
Zhang, Y.P., et al., "Regulation of Cellulase Synthesis in Batch and Continuous Cultures of Clostridium thermacellum", (2005) J. Bacteriol., 187(1):99-106.
Zheng, Y., et al., "Overview of biomass pretreatment for cellulosic ethanol production", (Sep. 2009) Int. J. Agric. & Biol. Eng., 2(3):51-67.
Zheng, H., et al., "Increase in Furfural Tolerance in Ethanologenic *Escherichia coli* LY180 by Plasmid-Based Expression of thyA", (2012) Appl. Environ. Microbiol., 78(12):4346-4352.
Mills, T.Y., et al. "Cellulosic hydrolysate toxicity and tolerance mechanisms in *Escherichia coli* ", (Oct. 15, 2009) Biotechnology for Biofuels, 2(26):1-11.

* cited by examiner

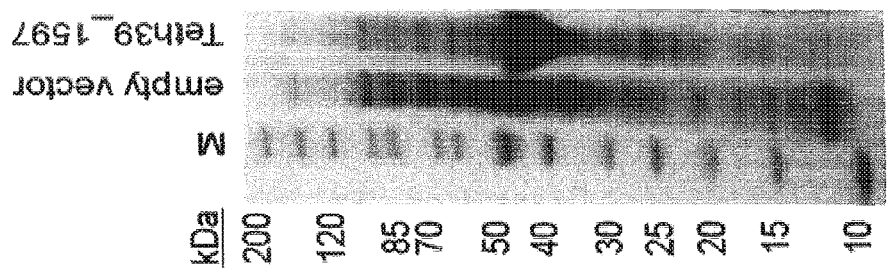
FIG. 6B
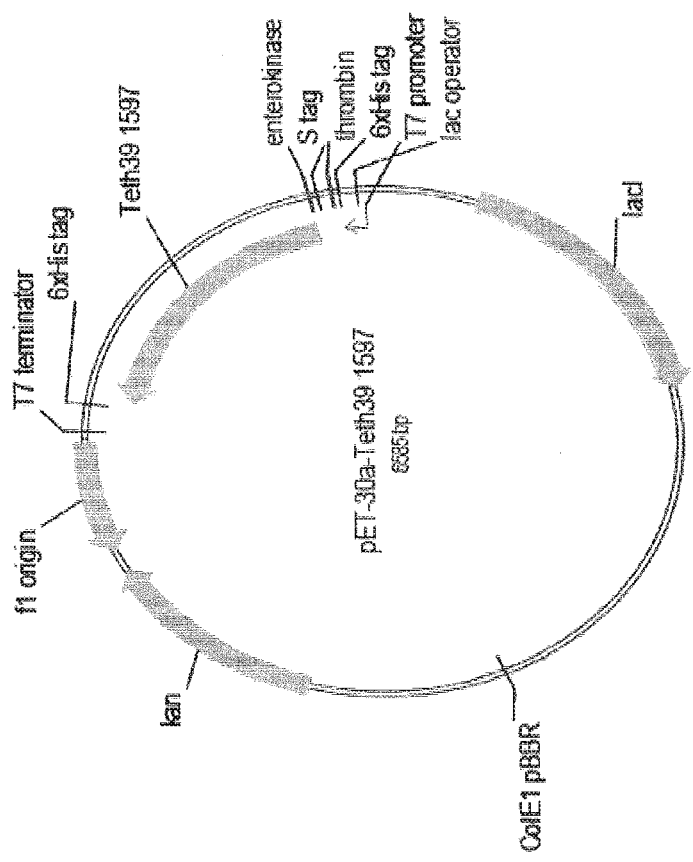
FIG. 6A
FIGS. 6A-6B

US 9,951,359 B2

HEAT-STABLE, FE-DEPENDENT ALCOHOL DEHYDROGENASE FOR ALDEHYDE DETOXIFICATION

This application is a divisional of U.S. patent application Ser. No. 14/310,725, filed Jun. 20, 2014, which claims the benefit of priority of U.S. Provisional Patent Application No. 61/838,961, filed Jun. 25, 2013, the contents of both of which are incorporated herein by reference.

This invention was made with government support under Prime Contract No. DE-AC05-00OR22725 awarded by the U.S. Department of Energy. The government has certain rights in the invention.

INCORPORATION BY REFERENCE OF SEQUENCE LISTING

The Sequence Listing in an ASCII text file, named 29661A_2933_1_SEQ_ST25.txt of 6 KB, created on Mar. 3, 2016, and submitted to the United States Patent and Trademark Office via EFS-Web, is incorporated herein by reference.

FIELD OF THE INVENTION

The present invention relates to microorganisms and polypeptides for detoxifying aldehydes associated with industrial fermentations. In particular, a heat-stable, NADPH- and iron-dependent alcohol dehydrogenase was cloned from *Thermoanaerobacter pseudethanolicus* 39E (Teth39E). The enzyme displayed activity against a number of aldehydes including inhibitory compounds that are produced during the dilute-acid pretreatment process of lignocellulosic biomass before fermentation to biofuels. The enzyme was introduced into and expressed in anaerobic, thermophillic microorganisms. Methods to use the microorganisms and polypeptides of the invention for improved conversion of biomass to biofuel are provided as well as use of the enzyme in metabolic engineering strategies for producing longer-chain alcohols from sugars using thermophilic, fermentative microorganisms.

BACKGROUND OF THE INVENTION

Lignocellulosic biomass represents one of the most abundant renewable resources on Earth. It is formed of three major components: cellulose, hemicellulose, and lignin, and includes, for example, agricultural and forestry residues, municipal solid waste (MSW), fiber resulting from grain operations, waste cellulosic products (e.g., paper and pulp operations), and energy crops. The cellulosic and hemicellulosic polymers of biomass can be hydrolyzed into their component sugars, such as glucose and xylose, which can then be fermented by microorganisms to produce ethanol. Conversion of even a small portion of the available biomass into ethanol could substantially reduce current gasoline consumption and dependence on petroleum.

Many conversion processes are known that breakdown lignocellulosic biomass to produce bioenergy. These processes vary from multi-enzyme and multi-fermentation approaches called separate hydrolysis and fermentation (SHF) [Wilke et al. (1976) Biotechnol. Bioeng. Symp. 6:55] to simpler, simultaneous cellulose hydrolysis (or saccharification) and fermentation (SSF) [Takagi et al. (1977) in Proceedings of the Bioconversion Symposium, Indian Institute of Technology, New Delhi, pp. 55-571; Spindler (1988) Appl. Biochem. Biotechnol.17:279-294; Alfani (2000) J. Ind. Microbiol. Biotechnol. 25:184-192]. In an SHF process, the cellulosic biomass is hydrolyzed with cellulases to liberate fermentable glucose followed by a separate step for fermentation to ethanol. The SSF process combines the enzymatic hydrolysis and fermentation simultaneously, reducing the process complexity. A natural extension is simultaneous saccharification and cofermentation (SSCF) using microorganisms that are able to convert both hexose and pentose sugars to ethanol. This process simplification culminates with the development of fermentation microorganisms that produce their own enzymes for cellulose hydrolysis, called consolidated bioprocessing (CBP). CBP involves four biologically-mediated events: (1) enzyme production, (2) substrate hydrolysis, (3) hexose fermentation and (4) pentose fermentation. In contrast to the other approaches, where some or all of the steps may be performed independently, all four events are performed simultaneously in a CBP configuration.

While chemical and physical pretreatment of lignocellulosic biomass improves substrate reactivity, it also produces microbial growth inhibitors such as furan and phenolic aldehydes [Klinke et al. (2004) *Appl. Microbiol. Biotechnol.* 66: 10-26]. The most abundant inhibitors, 5-hydroxymethyl furfural (5-HMF) and furfural, are generated from the dehydration of glucose and xylose, respectively, under acidic pH at high temperatures. These aldehydes impart broad cytological and physiological damage, especially in ethanologenic fungi and bacteria [Taylor et al. (2012) *Biotechnol. J.* 7:1169-1181; Palmqvist et al. (2000a) *Bioresource Technol.* 74:17-24]. Hence, for processes which involve fermentation, there is a need to abate the microbial inhibition that can arise during biomass pretreatment.

Several non-biological strategies have been described in the literature for removal of pretreatment inhibitors from lignocellulosic hydrolysates, including overliming with $Ca(OH)_2$ or NaOH to precipitate inhibitors and addition of activated charcoal or anion exchange resins to adsorb toxic compounds [Taylor 2012; Palmqvist et al. (2000b) *Bioresource Technol.* 74:25-33]. Biological abatement has been evaluated either by adding enzymes to hydrolysates to degrade compounds (generally specific for phenolic, lignin-derived inhibitors) or by adding microorganisms capable of directly metabolizing pretreatment inhibitors. For example, Li et al. showed that *Cupriavidus necator* can rapidly reduce furfural to the less toxic form, furfuryl alcohol [Li et al. (2011a) *Biodegradation* 22:1215-1225]. Conceptually, this microorganism could be applied to pretreatment hydrolysates to scavenge furan aldehydes; however, the microorganism requires oxygen for growth and does not grow at elevated temperatures, whereas many industrial processes are conducted at elevated temperatures under anaerobic conditions, making this microorganism unsuitable for such processes.

To improve inhibitor tolerance, fermentative, biofuel-producing microorganisms have been adapted or genetically modified to provide robust growth and performance in the presence of pretreatment hydrolysates. For example, improved inhibitor tolerance has been engineered into common ethanologenic microorganisms, including *Saccharomyces cerevisiae* [Almeida et al. (2007) *J. Chem. Technol. Biotechnol.* 82:340-349; Larsson et al. (2001) *Appl. Environ. Microbiol.* 67:1163-1170], *Zymomonas mobilis* [Yang et al. (2010) *Bmc Microbiol.* 10:135)], and ethanologenic *Escherichia coli* [Wang et al. (2011) *Appl. Environ. Microbiol.* 77:5132-5140; Wang et al. (2012) *Appl. Environ. Microbiol.* 78:2452-2455; Zheng et al. (2012) *Appl. Environ. Microbiol.* 78:4346-4352]. Further, enzymatic detoxification of furan aldehydes has been widely documented in yeast [Liu et al. (2004) *J. Ind. Microbiol. Biotechnol.* 31:345-352; Bowman et al. (2010) *Appl. Environ. Microbiol.* 76:4926-4932; Park et al. (2011) *Bioresource Biotechnol.* 102:6033-6038] and in *E. coli* [Miller et al. (2009) *Appl. Environ. Microbiol.* 75:4315-4323; Wang et al. (2011)], which generally include aldehyde-specific oxidoreductases or alcohol dehydrogenases. While these microorganisms have been important for first-generation ethanol production, they are not suitable for second generation biofuels which use thermophilic, cellulolytic strains that can directly solubilize cellulose and ferment carbohydrates into fuels under anaerobic conditions [Elkins et al. (2010) *Curr. Opin. Biotechnol.* 21:657-662; Lynd, L. R. et al. (2008) *Nat. Biotechnol.* 26:169-172; Olson et al. (2012) *Curr. Opin. Biotechnol.* 23:396-405)].

Hence a need remains for anaerobic, inhibitor-tolerant microorganisms capable of fermentation at elevated growth temperatures (typically above 50-60° C., and even as high as 80° C.). To address this need, the saccharolytic thermophile *Thermoanaerobacter pseudethanolicus* 39E (Teth39E) was grown in the presence and absence of furfural and a protein that was up-regulated 7-fold was selected for further study. From the genomic sequence of Teth39E, this protein was identified as the product of open reading frame (orf) Teth39_1597 (hereinafter referred to as "the bdhA gene" or "bdhA") and found to encode an iron-dependent alcohol dehydrogenase (hereinafter referred to as "BdhA").

Alcohol dehydrogenases (ADHs) constitute a large family of enzymes and catalyze the reversible oxidation of primary or secondary alcohols to aldehydes or ketones. In bacteria and yeast, ADHs (also referred to herein and in the literature as aldehyde reductases) have been found that are capable of reducing furfural and 5-(hydroxymethyl) furfural (5-HMF) (and other toxic aldehydes) to alcohols. However, those enzymes which have heretofore been studied are distinct from that encoded by the bdhA gene.

For example, *S. cerevisiae* has multiple NADH and NADPH-dependent aldehyde reductases that can convert furfural and 5-HMF to non-toxic alcohols [Liu et al. (2008) *Appl. Environ. Microbiol.* 81:743-753]. The *S. cerevisiae* ADH6 gene product has been characterized as a Zn- and NADPH-dependent enzyme capable of reducing 5-HMF (Larroy et al. (2002) *Biochem. J.* 361:163-172; Petersson et al. (2006) *Yeast* 23:455-464). U.S. Patent Appln. Pub. No. 2007/0155000 also describes ethanol-producing *S. cerevisiae* strains that tolerate furfural and 5-HMF by overexpressing the yeast ADH6 gene. U.S. Pat. No. 8,110,387 describes *S. cerevisiae* ADH1 and mutants thereof that have NADH-dependent 5-HMF reductase activity and indicates that these enzymes can aid in detoxifying lignocellulosic hydrolysates. U.S. Pat. No. 7,253,001 relates to *S. cerevisiae* strains with improved xylose utilization which were created by deleting an endogenous aldehyde dehydrogenase gene and introducing 5 other genes. U.S. Patent Appln. Pub. No. 2012/0190089 describes recombinant yeast with engineered metabolic pathways to produce isobutanol, in part by expressing an exogenous NADH-dependent ADH that converts isobutyraldehyde to isobutanol under anaerobic conditions. None of these yeast genes are homologous to BdhA.

U.S. Pat. No. 8,039,239 describes recombinant *Clostridia* strains that overexpress an NADPH-dependent secondary alcohol dehydrogenase with sequence homology to a previously-characterized *T. pseudethanolicus* NADPH-dependent alcohol dehydrogenase (Teth39 _0218). However, as shown in FIG. 4 of the '239 patent, the amino acid sequence of that ADH is markedly distinct from BdhA.

ADHs distinct from BdhA also exist in other bacteria. For example, U.S. Patent Appln. Pub. No. 2011/0177579 describes a thermostable, primary-secondary ADH from *Thermococcus guaymasensis* which appears related to Zn-dependent ADHs and it is unknown whether the enzyme is capable of detoxifying furfural or 5-HMF. U.S. Patent Appln. Pub. No. 2012/0108855 reports recombinantly-produced, ethanologenic bacteria with increased expression of the transhydrogenase genes pntA and pntB which are capable of imparting increased furfural tolerance. The *C. necator* strain mentioned above turns out to have a NADH- and Zn-dependent ADH [Li et al. (2011b) *Biodegradation* 22:1227-1237].

In accordance with the invention, the discovery of BdhA provides a route to modified anaerobic, aldehyde-tolerant thermophilic microorganisms suitable for use in bioprocessing lignocellulosic biomass to efficiently produce biofuel.

SUMMARY OF THE INVENTION

The present invention provides isolated microorganisms that express an exogenous heat-stable, NADPH- and iron-dependent alcohol dehydrogenase cloned from *Thermoanaerobacter pseudethanolicus* 39E, or a homolog thereof.

In one embodiment, the present invention provides isolated anaerobic, thermophilic microorganisms that can be used in one or more bioprocessing steps for conversion of biomass to biofuel, including the processes of SHF, SSF, SSCF and CBP, that have been engineered to express an exogenous heat-stable, NADPH- and iron-dependent alcohol dehydrogenase cloned from *Thermoanaerobacter pseudethanolicus* 39E, or a homolog thereof, at expression levels that impart aldehyde tolerance to the microorganism. Preferred microorganisms include, but are not limited to, *Thermoanaerobacter* spp., as well as anaerobic, thermophilic Firmicutes species, especially *Clostridia* and *Caldicellulosiruptor* spp., and the like.

In another aspect of the invention, bacterial cell lysates are prepared from the microorganisms of the present invention. Such lysates include whole cell lysates and lysates in which the bacterial membranes have been removed (e.g., by centrifugation) to provide clarified supernatants. Whole cell lysates of the invention have active exogenous heat-stable, NADPH- and iron-dependent alcohol dehydrogenase cloned from *Thermoanaerobacter pseudethanolicus* 39E, or a homolog thereof which, in the presence of NADPH, have an aldehyde reductase specific activity of at least about 2-20 µmol/min/mg with furfural as a substrate, of at least about 5-50 µmol/min/mg with 5-HMF as a substrate, of at least about 2-20 µmol/min/mg with acetaldehyde as a substrate, 0.3-3 µmol/min/mg with isobutyraldehyde, and/or at least about 7-70 µmol/min/mg with butyraldehyde as a substrate. In preferred embodiments, the aldehyde reductase specific activity with NADPH as a cofactor is at least 4 µmol/min/mg with furfural as a substrate, at least 10 µmol/min/mg with 5-HMF as a substrate, of at least 4 µmol/min/mg with acetaldehyde as a substrate, at least 0.6 µmol/min/mg with isobutyraldehyde, and/or at least 14 µmol/min/mg with butyraldehyde as a substrate.

Yet another aspect of the invention relates to an isolated polypeptide comprising NAD(P)H- dependent and iron-dependent aldehyde reductase activity, and being at least 70, 80, 90 or 95% identical to the amino acid sequence set forth in SEQ ID NO: 2. In some embodiments the polypeptide is at least 98 or 99% identical to the amino acid sequence in SEQ ID NO: 2, and in other embodiments, the polypeptide has the amino acid sequence in SEQ ID NO: 2 or consists essentially of the amino acid sequence in SEQ ID NO: 2, and can include modification such as His tags to allow rapid purification of the protein.

The invention further provides an isolated and purified nucleic acid encoding any of the polypeptides of the invention, recombinant expression vectors comprising a nucleic acid of the invention and host cells comprising the vectors of the invention. Such host cells include strains typically used in cloning and protein expression, such as *E. coli*, as well as thermophilic, anaerobic hosts that are suitable for use in at least one step of an industrial fermentation process.

In some aspects, the isolated and purified nucleic acid is at least 70, 80, 90 or 95% identical to the nucleic acid sequence set forth in SEQ ID NO: 1. In some embodiments the isolated and purified nucleic acid is at least 98 or 99% identical to the nucleic acid sequence in SEQ ID NO: 1, and in other embodiments, the isolated and purified nucleic acid has the nucleic acid sequence in SEQ ID NO: 1 or consists essentially of the nucleic acid sequence in SEQ ID NO: 1.

In accordance with the invention, the anaerobic, thermophilic microorganisms and proteins of the invention can be used in biomass fermentation processes to detoxify aldehydes that are present in the biomass (e.g., produced by acid pretreatment or during fermentation). Detoxification of aldehydes, as used herein, means a reduction in aldehyde content below the level that normally inhibits growth of a particular (unmodified) microorganism for any particular aldehyde, and thereby making the microorganism aldehyde tolerant and allowing improved biofuel yield when that microorganism is used in a fermentation step. Hence, the invention provides methods of improving yield and/or efficiency of biomass conversion to biofuel by contacting biomass with an anaerobic, thermophilic microorganism of the invention, a protein of the invention, or a cell lysate of the invention for a time and under thermophilic, anaerobic conditions sufficient to detoxify inhibitory aldehydes that may be present in the biomass. The method is used with biomass before or during SHF, SSF, SSCF or CBP, and can further be used with biomass that has been pretreated by dilute acid, hot water only or enzymatic hydrolysis.

A still additional aspect of the invention provides a method to produce butanol from biomass which comprises culturing biomass with an anaerobic, thermophilic microorganism of the invention for a time and under fermentation conditions suitable to produce butanol and recovering said butanol. The invention also contemplates similar methods for producing ethanol, furfuryl alcohol, and/or 2,5-(dihydroxymethyl)furan, by culturing as for butanol production and recovering the desired alcohol. Depending on the source of biomass, certain alcohols may predominate over others, for example, using the method with furan waste from pulp or paper processing is advantageous for recovering furfuryl alcohol

BRIEF DESCRIPTION OF THE DRAWINGS

FIG. 6A presents a schematic diagram of the plasmid pET-30a-Teth39_1597 which has the Teth39_1597 coding sequence (the bdhA gene) under inducible control of a strong T7 promoter (when grown with IPTG) via the lac operon present on the plasmid. FIG. 6B shows a Coomassie-blue stained, SDS-PAGE gel of cell lysates after addition of IPTG to *E. coli* clones carrying pET-30a-Teth39_1597 or a control plasmid. M., molecular weight markers.

FIG. 11A shows PCR products amplified from the targeted chromosome region in JWCB001 (wild type; lane 1), JWCB018 (pyrAF ldh$^-$ cbel; lane 2), JWCB044 (pyrAF ldh$^-$ cbel Teth39_1957$^+$; lane 3), and no DNA (lane 4) with primers DC477 and DC478. Total cell protein (80 µg) was isolated from mid-log phase cultures and electrophoresed in SDS-PAGE gels either for staining with Coomassie Brilliant Blue (FIG. 11B) or for Western blot analysis (FIG. 11C) probed with an anti-His antibody. Lane 1: JWCB001 (wt) grown at 75° C.; lane 2: JWCB018 grown at 75° C.; lane 3: JWCB044 grown at 65° C.; lane 4: JWCB044 grown at 70° C.; lane 5: JWCB044 grown at 75° C.

DETAILED DESCRIPTION OF THE INVENTION

The present invention relates to engineered anaerobic, thermophilic microorganisms used in industrial fermentations that express an exogenous heat-stable, NADPH- and iron-dependent alcohol dehydrogenase cloned from *Thermoanaerobacter pseudethanolicus* 39E (Teth39E), or homologs thereof. In one embodiment, the exogenous heat-stable, NADPH- and iron-dependent alcohol dehydrogenase cloned from Teth39E is the gene product of the Teth39_1597 locus.

By engineering anaerobic, thermophilic microorganisms to express exogenous heat-stable, NADPH- and iron-dependent alcohol dehydrogenase cloned from *Thermoanaerobacter pseudethanolicus* 39E (Teth39E), or homologs thereof, or by adding the expressed proteins to industrial hydrolysis and fermentation, allows improved efficiency and/or yield for conversion of biomass to biofuel by detoxifying pretreatment inhibitors found in such industrial fermentations.

The substrate specificity of the heat-stable, NADPH- and iron-dependent alcohol dehydrogenase cloned from Teth39E for aldehydes includes furfural, 5-hydroxymethylfurfural (5-HMF), isobutyraldehyde, butyraldehyde, and acetaldehyde, which the enzyme converts to alcohols (see FIGS. 1A, 1B, 2A, and 3, and Table 1).

BdhA Proteins, Nucleic Acids and Expression Vectors

Figure 4:
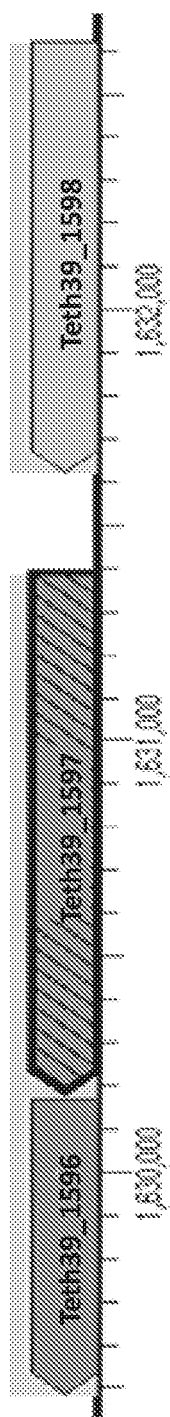
FIG. 4 shows a cartoon depicting three Teth39E open reading frames, Teth39_1596, Teth39_1597 and Teth39_1598. Teth39_1597 encodes an Fe-dependent alcohol dehydrogenase, the expression of which is upregulated approximately 7-fold when Teth39E is cultured in medium containing 15 mM furfural.
Figure 5:
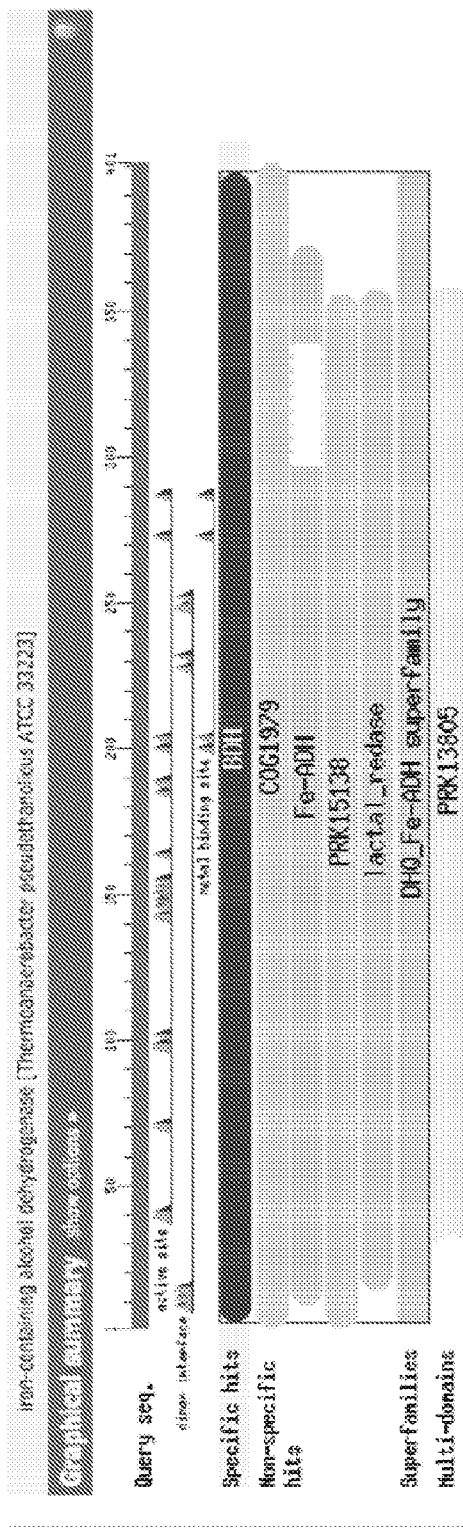
FIG. 5 presents results of homology analysis of the bdhA gene sequence using the BLAST Conserved Domain Database at the National Center for Biotechnology Information and shows that the bdhA gene contains a butanol dehydrogenase (BDH) domain involved in the conversion of butyraldehyde to butanol using NAD(P)H.

Teth39_1597 is the locus tag for an iron-containing alcohol dehydrogenase encoded by *Thermoanaerobacter pseudethanolicus* strain ATCC 33223 (abbreviated herein as Teth39E). Teth39E increases expression of an iron-dependent alcohol dehydrogenase (BdhA) when grown in the presence of furfural. The open reading frame encoding Teth39_1597 is located at positions 1,630,187 to 1,631,392 on the chromosome of Teth39E (see FIG. 4), is 1206 bp in length (SEQ ID NO: 2) and encodes a protein of 401 amino acids (SEQ ID NO: 1) with a mass of approximately 43.4 kD. The gene product belongs to the family of iron-containing alcohol dehydrogenases and possesses highly conserved domains for butanol dehydrogenase, an enzyme which can catalyze the final step in butanol formation in anaerobic bacteria (see FIG. 5). The iron-dependent alcohol dehydrogenases have higher activity for longer chain aldehydes relative to formaldehyde or acetaldehyde. For BdhA it is shown herein that the substrate preference in whole lysates with NADPH as the cofactor, from most to least activity, is butyraldehyde, 5-HMF, furfural, acetaldehyde and isobutyraldehyde (see Table 1).

Enzymatic activity can be measured in the forward or reverse reaction direction, by alcohol to aldehyde conversion (dehydrogenation) or by aldehyde to alcohol conversion (reduction) using methods known in the art. For alcohol conversion to aldehyde, the enzymatic activity of BdhA is said to be an alcohol dehydrogenase activity. For aldehyde conversion to alcohol, the enzymatic activity of BdhA is said to be an aldehyde reductase activity. BdhA and its homologs can be characterized by specifying either activity. The specific activity of BdhA with NADPH as a cofactor is at least 0.5 μmole/min/mg when expressed in *E. coli* and measured with various aldehydes in a whole cell lysate. When butyraldehyde is the substrate, the specific activity can reach to at least about 14 μmole/min/mg.

As used herein, "nucleic acid" includes RNA and DNA in any form, including in single or double stranded form and as cDNA. Isolated nucleic acid means that the nucleic acid has been removed from its natural position in the genome (or on an epichromosomal element such as a natural plasmid) and that it has a discrete size and can be a fragment or circular molecule in a useful form for manipulation such as for a probe, for creating a mutation, for use in cloning particular sequences, for protein expression and for such other recombinant and molecular biology techniques as known in the art.

Purified nucleic acids or proteins are preparations of nucleic acids or proteins, respectively, that within reasonable detection limits, form a homogenous preparation of that particular molecule. The preparation may contain buffer or other non-nucleic acid or non-proteinaceous components routinely used in such purifications and manipulations. For example, a restriction fragment purified from an agarose gel is considered an isolated and purified nucleic acid. Likewise, a protein excised from a polyacrylamide gel is considered an isolated and purified protein. As used herein, "substantially purified" or "partially purified" molecules are at least 60% free, at least 75% free, or at least 90% free from other components with which they are naturally associated. As used herein, the terms "purified" and "to purify" also refer to the removal of contaminants from a sample. The removal of contaminating molecules results in an increase in the percent of polypeptide or nucleic acid of interest in the sample.

One aspect of the invention is directed to isolated nucleic acids and expression vectors that encode the polypeptides of the present invention, that are used to create isolated anaerobic, thermophilic microorganisms that express an exogenous BdhA, or a homolog thereof.

Expression vectors suitable for use in the present invention comprise nucleic acids encoding exogenous BdhA, or a homolog thereof, operably linked to a promoter, preferably a strong inducible promoter, to allow expression of the exogenous BdhA, or a homolog thereof in the microorganisms of the present invention.

Expression vectors suitable for use in the present invention contain appropriate regulatory sequences, such as a promoter and operator, so that the microorganism host-cell machinery can transcribe the exogenous gene and translate the resultant messenger RNA to synthesize the corresponding exogenous protein. In certain embodiments, the regulatory sequences are specific for the microorganism into which the expression vector is introduced. In certain embodiments, the expression vector is a plasmid. In alternate embodiments, the expression vector is a virus. In certain embodiments, the exogenous gene integrates into the host cell genome.

In certain embodiments, flanking sequences in the vector upstream and downstream of the exogenous gene enhances integration of the exogenous gene into the host cell genome.

In certain embodiments, the expression vector contains sequences that introduce modifications to the exogenous gene. The modifications may include post-translational modifications (e.g., glycosylation, methylation), purification tags (e.g., a His tag) or reporter moieties to facilitate purification, manipulation and characterization of the protein. Such modifications are not included in calculations of sequence identities.

The methods for making such expression vectors as well as useful vectors and promoters therefor, along with additional expression control elements and purification tags, are all well known in the art and can be readily made and used by those of skill in the art. In general, molecular biological techniques for cloning and protein expression can be found in Green & Sambrook (2012) Molecular Cloning, A Laboratory Manual, 4th ed., Cold Spring Harbor Press, NY.

For protein expression in Gram positive thermophiles, useful shuttle and expression vectors include, but are not limited to, pNW33N, pMK3, pMK4 (from the Bacillus Genetic Stock Center), pIKM1 [Mai et al. (1997) FEMS Microbiol. Let. 148:163-167]; and, pDCW142 [Chung et al.

(2014) PNAS, 111:8931-8936] and pDCW89 [Chung et al. (2013) PLoS ONE 8(5): e62881. doi:10.1371/journal.pone.0062881].

In one embodiment, *Caldicellulosiruptor bescii* is engineered to express an exogenous heat-stable, NADPH- and iron-dependent alcohol dehydrogenase cloned from *Thermoanaerobacter pseudethanolicus* 39E, or a homolog thereof, using the expression/integration vector disclosed in Chung et al. [PNAS, 2014, 111:8931-8936].

In one embodiment, *Caldicellulosiruptor bescii* is engineered to express an exogenous heat-stable, NADPH- and iron-dependent alcohol dehydrogenase cloned from *Thermoanaerobacter pseudethanolicus* 39E, or a homolog thereof, using the expression/integration vector disclosed in Chung et al. [PLoS ONE 8(5): e62881. doi:10.1371/journal.pone.0062881].

*E. coli* is a common organism to use for protein production and techniques to express heterologous proteins in *E. coli* are well known.

Introduction of the expression vector into a host cell may be via any suitable method that is readily selected by one of skill in the art. Examples include the methods disclosed in Chung et al, and Cha et al. [Biotechnology for Biofuels, 2013, 6:85].

The expressed exogenous BdhA, or a homolog thereof, can be expressed in bacteria, yeast, or mammalian host cells. The exogenous BdhA, or a homolog thereof, may be recovered to provide isolated and/or purified polypeptides after the removal of host cell proteins. Alternatively, the host cell containing the expression vector may be used in the production of bulk and platform chemicals from lignocellulosic material, such as lignocellulosic feedstock, where there is a need to detoxify 5-HMF, other furans or other aldehydes or carbonyl compounds.

Accordingly, one aspect of the invention provides an isolated polypeptide that comprises BdhA or is a homolog thereof. A BdhA homolog is a protein with NAD(P)H- and iron-dependent aldehyde reductase activity and has, over the course of the BdhA amino acids, at least 70, 80, 90, 95, 98 or 99% identity to the amino acids encoded by the bdhA gene, and preferably has at least 90, 95, 98 or 99% amino acid identity. Enzymatic activity can be measured in the forward or reverse reaction direction, by alcohol to aldehyde conversion (dehydrogenation) or by aldehyde to alcohol conversion (reduction) using methods known in the art. For alcohol conversion to aldehyde, the enzymatic activity of BdhA or a homolog thereof is said to be an alcohol dehydrogenase activity. For aldehyde conversion to alcohol, the enzymatic activity of BdhA or a homolog thereof is said to be an aldehyde reductase activity. BdhA or a homolog thereof can be characterized by specifying either activity. The specific activity of BdhA or a homolog thereof with NADPH as a cofactor is at least 0.5 µmole/min/mg when expressed in *E. coli* and measured with various aldehydes in a whole cell lysate. When butyraldehyde is the substrate, the specific activity can reach to at least about 14 µmole/min/mg. The amino acid sequence of BdhA is set forth in SEQ ID No: 2. Examples of algorithms that are suitable for determining percent sequence identity and sequence similarity, such as the BLAST algorithm, are well known to those skilled in the art. If additional amino acids are present, such as a His tag for purification, these amino acids are not factored in the identity calculation.

The isolated polypeptides of the invention can also be purified to varying degrees of homogeneity and preparations which range to at least 30, 40, 50, 60, 70, 80, 90, 95, 99 and 99.9 percent homogenous are within the ambit of the invention. Techniques for purifying proteins are known in the art and protein purity can be assessed by various known methods, including but not limited to, SDS-PAGE, increase in specific activity, amino acid analysis, amino acid sequence analysis and combinations thereof.

The polypeptides of the invention can be used in the production of bulk and platform chemicals from lignocellulosic material, such as lignocellulosic feedstock, where there is a need to detoxify 5-HMF, other furans or other aldehydes or carbonyl compounds. Examples of biofuels and bulk and platform chemicals include ethanol, butanol, lactate, 1,4-dicarboxylic acids (succinic, fumaric, malic), glycerol, sorbitol, mannitol, arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone, fatty acids, fatty-derived molecules, isoprenoids, isoprenoid-derived molecules, alkanes, isopentanol, and isoamylacetate. When using the polypeptides of the invention, increased specific productivity (gram product per gram cell and hour) can be achieved due to the faster removal of inhibitory furan compounds and carbonyl compounds from the medium.

Thus, the polypeptides of the invention are useful to reduce the aldehyde content of biomass and to allow microorganisms that are normally inhibited at high aldehyde concentration to be used in fermentation steps. For example, the polypeptides can be mixed with biomass for a time and under conditions to convert the aldehydes that are present in the biomass (or that are released as the biomass is hydrolyzed) to non-toxic alcohols. The proteins can be added before any fermentation steps or during one or more fermentation steps to provide more efficient conversion of biomass to biofuel. The proteins of the invention are particularly useful in conjunction with anaerobic, thermophilic fermentations due to their thermostability.

Microorganisms

The invention generally provides two groups of microorganisms that express a polypeptide of the invention: (1) anaerobic, thermophilic microorganisms used in at least one step of an industrial fermentation process and which express an exogenous BdhA or a homolog thereof; and (2) microorganisms used in cloning, expression and purification of BdhA or a homolog thereof.

As used herein "exogenous expression" refers to the expression of a gene product from a gene that has been introduced into a subject microorganism. The introduced gene may be a heterologous gene (i.e. not present in the subject microorganism), or identical or homologous to an endogenous gene in the subject microorganism.

As used herein, "exogenous BdhA" or "exogenous BdhA or a homolog thereof" refers to the expression of BdhA or a homolog thereof from a gene that has been introduced into a subject microorganism. The introduced gene may be a heterologous gene (i.e. not present in the subject microorganism), or identical or homologous to an endogenous gene in the subject microorganism.

The term "thermophiles" refer to microorganisms that can grow in high temperature environments, for example, at temperatures of at least 50° C. or more. Thermophiles have growth optima that range between 50 and 100° C. The genome and proteome composition of thermophiles are characterized by overrepresentation of purine bases in protein coding sequences, higher GC-content of structural RNAs, distinct synonymous codon usage, enhanced usage of positively charged residues and aromatic residues, and a decrease in polar uncharged residues in the encoded protein.

Thermophiles have optimal growth temperatures above 50° C., and typically between about 50-60° C. Extreme thermophiles have optimal growth temperatures above 65° C. and typically between about 70-80° C. Often extreme thermophiles are capable of growing at the temperatures used for thermophilic microorganisms.

Anaerobic, thermophilic microorganisms that are used in at least one step in industrial fermentations are capable of, or have been engineered to be capable of, one or all of the steps of hydrolyzing cellulose and hemicellulose and converting the resultant hexose and pentose sugars, including xylose, to ethanol and acetic acid for a bioenergy source. Additionally, in accordance with the invention, this group of microorganisms can be recombinantly engineered to express exogenous BdhA or homolog thereof. Such strains can be made by techniques known in the art.

Introduction of the expression vector into a host cell may be via any suitable method that is readily selected by one of skill in the art. Examples include the methods disclosed in Chung et al, Cha et al, U.S. Patent Application Publication No. 2008028340, Tripathi et al. [2010, Appl, Environ. Microbiol. 76:6591-6599], and Argyros et al. [2011, Appl, Environ. Microbiol. 77:8288-8294].

Many classes of anaerobic, thermophilic bacteria are available for many purposes and stages in industrial fermentations. Cellulolytic microorganisms are capable of hydrolyzing cellulose. These bacteria produce cellulase which hydrolyzes cellulose to produce glucose. Many examples of cellulolytic, thermophilic microorganisms are known. Hemicellulolytic microorganisms produce xyalanases and are thus capable of hydrolyzing hemicellulose to release pentose sugars, especially xylose, that can then be further fermented. Useful reviews describing cellulolytic thermophiles and/or hemicellulolytic (extreme) thermophiles include, for example, Bergquist et al. (1999) FEMS Microbiol. Ecol. 28:99-110; Lynd et al. (2002) Microbiol. Mol. Biol. Rev. 66:506-577; Vanfossen et al. (2008) Ann. NY Acad. Sci. 1125:322-37. Some specific microorganisms described and known include, the cellulolytic thermophile *Clostridium thermocellum* [Raman et al. (2009) PLoS ONE 4(4): e5271 (2009); Zhang et al. (2005) J. Bacteriol. 187: 99-106; Raman et al. (2011) BMC Microbiol. 11:134] and *Clostridium thermohydrosulfuricum* [Lovitt et al. (1984) App. Microbiol. 48:171-177]; as well as the hemicellulolytic extreme thermophiles including various *Caldicellulosiruptor* spp. [Blumer-Schuette et al. (2008) Curr. Opin. Biotechnol. 19:210-217; Blumer-Schuette et al. (2010) App. Microbiol. 76:8084-8092; Blumer-Schuette et al. (2011) J. Bacteriol. 193:1483-4; pub March 2011; e-published Jan. 7, 2011] and more specifically *Caldicellulosiruptor obsidiansis* [Hamilton-Brehm et al. (2010) App. Environ. Microbiol. 76:1014-1020; Mielenz et al. (2010) Abstract from "The 32nd Symposium on Biotechnology for Fuel and Chemicals" (Apr. 19-22, 2010)].

These microorganisms are useful in the SHF, SSF, SSCF and CBP industrial processes as described below. Furthermore, CBP microorganisms are needed that produce ethanol as sole product, hydrolyze cellulose to fermentable oligomers, hydrolyze hemicellulose to fermentable oligomers, ferment cellulose oligomers, ferment xylose or xylose oligomers, produce ethanol in high titer (resistant to up to 4 to 5% ethanol), be resistant to up to 1% acetic acid from hemicelluloses, grow at thermophilic temperatures ranging from 55 to 80° C., are moderately resistant to common pretreatment inhibitors (furans, polyphenolics) and produce a multi-carbohydrase portfolio on the cellulosome [Mielenz (2009) in *Molecular Biology and Biotechnology*, 5th Edition, Ed. J. M. Walker & R. Rapley, Royal Society of Chemistry, pp: 548-584]. No such single microorganism is presently known and the present invention addresses the resistance to pretreatment inhibitors by allowing genetic engineering of appropriate CBP microorganisms to express exogenous BdhA or homologs thereof active at reducing common pretreatment inhibitors such as furfural and 5-HMF.

Additionally, metabolic engineering of microorganisms (altering specific fermentative pathways in a microorganism) is being used to direct microorganisms to preferentially or exclusively produce particular biofuels from sugar substrates. Thus exogenous BdhA or homologs thereof can be incorporated in such strategies to produce anaerobic, thermophilic microorganisms of the invention capable of producing a particular biofuel of interest such as ethanol, butanol, isobutanol and the like.

Accordingly, in some embodiments, the anaerobic thermophiles of the invention which have been modified to express exogenous BdhA or a homolog thereof are *Clostridium* species. Examples of useful *Clostridium* spp., *C. thermocellum*, *C. straminisolvens*, and *C. thermocopriae*, with *C. thermocellum* being a preferred organism. *C. thermocellum* is an established bacterium for hydrolysis of cellulose in the biofuel production process. Its growth temperature range is 45-65° C. and it grows optimally at 60° C. *C. thermocellum* strains that express exogenous Teth39_1597 or a homolog thereof may be used in methods to produce n-butanol, furfural, and the other alcohols from when aldehydes are reduced by this enzyme.

In other embodiments, the anaerobic thermophiles of the invention which have been modified to express exogenous BdhA or a homolog thereof are *Caldicellulosiruptor* species. *Caldicellulosiruptor* spp. are extremely thermophilic, anaerobic, Gram-positive bacteria capable of hydrolyzing hemicellulose and exhibit optimal growth in the temperature range of 70-80° C. The members of this genus are also capable of cofermentation of pentose and hexose sugars, including xylose. The *Caldicellulosiruptor* spp. suitable for use in the present invention include *C. bescii*, *C. saccharolyticus*, *C. hydrothermalis*, *C. kristjanssonii*, *C. kronotskyensis*, *C. lactoaceticus*, *C. owensensi*, *C. acetigenus* and *C. obsidiansis*. *C. bescii* is a preferred species.

*Caldicellulosiruptor obsidiansis* (*C. obsidiansis*) is an extreme thermophile isolated from Yellowstone National Park (Hamilton-Brehm 2010). *C. obsidiansis* grows optimally at 78° C. and primarily produces acetic acid and lower levels of ethanol. It readily hydrolyzes hemicellulose and to a slower degree, hydrolyzes cellulose.

In other embodiments, the anaerobic thermophiles of the invention which have been modified to express exogenous BdhA or a homolog thereof are *Thermoanaerobacter* and *Thermoanaerobacterium* species and *T. pseudethanolicus* strains *Thermoanaerobacter* and *Thermoanaerobacterium* species, include but are not limited to *Thermoanaerobacter brockii* (sample strain: ATCC 35047), *Thermoanaerobacter ethanolicus* (sample strain: JW200 DSM 2246), *Thermoanaerobacter pseudethanolicus* (sample strain: 39E ATCC 33223), *Thermoanaerobacterium aotearoense* (sample strain: DSM 10170), *Thermoanaerobacterium saccharolyticum* (sample strains include B6A, B6A-RI ATCC 49915, and JW/SL-YS485 DSM 8691), *Thermoanaerobacterium thermosaccharolyticum* (sample strains include ATCC 7956, HG-8 ATCC 31960, M0523, M0524 and M0795) and *Thermoanaerobacterium xylanolyticum* (sample strain: DSM 7097).

Genetic transformation of *Thermoanaerobacter* and *Thermoanaerobacterium* species is described in Shaw et al. (2010) Appl. Environ. Microbiol. 76:4713-4719.

In certain embodiments, the present invention provides microorganisms for cloning and expressing exogenous BdhA or a homolog thereof. Such microorganisms include bacteria, yeast and fungi, as well as cells, such as mammalian cells or insect cells. As discussed above in the section on BdhA Proteins, Nucleic Acids and Expression Vectors, hosts are well known in the art and include *E. coli, S. cerevisiae* and the like.

Cell Lysates

Yet another aspect of the invention is drawn to cell lysates prepared from the microorganisms of the invention. Cell lysates comprise active BdhA polypeptides and can thus be used directly to reduce the aldehyde content of biomass. On the industrial scale, cell lysates can be grown in large fermentor vessels. Once the appropriate cell density is achieved with an appropriate level of BdhA aldehyde reductase activity, the cells are harvested and lysed. Lysing can be by physical treatment, by chemical treatment, by enzymatic treatment or a combination thereof. Once lysed, the mixture can be used directly with biomass. Alternatively, the cellular debris and membranes can be removed by centrifugation and the remaining supernatant (which has the BdhA aldehyde reductase activity) can be used in a method of the invention.

Methods

In accordance with the invention, the anaerobic, thermophilic microorganisms and proteins of the invention are useful to detoxify aldehydes that are present in biomass, especially in lignocellulosic biomass pretreated with acid as used in many industrial fermentation processes to produce one or more biofuels. Hence, this invention provides a method of improving yield and/or efficiency of biomass conversion to biofuel by contacting biomass with an anaerobic, thermophilic microorganism of the invention, a polypeptide of the invention or a cell lysate of the invention for a time and under thermophilic, anaerobic conditions sufficient to detoxify inhibitory aldehydes present in said biomass, and thereby produce improved yields or efficiency of biomass conversion to biofuel, relative to biomass that has not been so treated, when the so-treated biomass is used in industrial fermentation processes.

Generally, the aldehyde detoxification treatments of the invention occur after hydrolysis of biomass, since that is when aldehydes are generated. However, the aldehyde detoxification treatments of biomass can be conducted before or during SHF, SSF, SSCF or CBP fermentation steps. If the hydrolysis steps that produce aldehydes occur simultaneously with a fermentation step or are conducted by microorganisms, then the aldehyde detoxification treatments can also be conducted simultaneously with those steps. In a preferred method, the biomass is pretreated with acid, then simultaneously treated for aldehyde detoxification and fermented with one or more microorganisms to produce biofuels.

The ethanol and acetic acid (and other fermentation by-products which can supply energy) from industrial fermentations are referred to as biofuel. Biofuel derives its energy from biological carbon fixation and covers many types of energy sources including ethanol, butanol, biodiesel (produced from biological oils and fats), bioethers, biogas (methane) and even biomass (when used in combustion processes). As used herein, biofuel includes, but is not limited to, one or more of the energy-yielding molecules produced by the biological hydrolysis and fermentation of biomass. For example, biofuel obtained from biomass includes 2-4 carbon atom alcohols, such as ethanol, butanol, isobutanol, as well as acetate, and is not limited to any particular combination of products that are produced, e.g., such as ethanol and acetic acid, singly or in combination. Ethanol is sometimes referred to as bioethanol, cellulosic ethanol, corn ethanol and other names, which may typically reflect the source from which the ethanol is obtained. Ethanol has the chemical formula $CH_3CH_2OH$, no matter its source or production method.

Biomass is a renewable resource and has three main structural components—typically, 33-50% cellulose, 17-35% hemicellulose and 12-24% lignin—with the remainder being minerals, protein and other minor materials. Biomass is primarily lignocelluosic plant material but may include non-plant waste materials such as animal waste. Hence, "biomass" as used herein, includes, but is not limited to, forestry residue, agricultural residue, municipal solid waste (MSW), animal waste, yard waste, wood products, fiber resulting from grain operations, waste cellulosic products (e.g., paper and pulp operations), grasses, and energy crops whether grown for biomass production or for other purposes. The embodiments of the invention can use any type of biomass, alone or in any combination or in any ratio. It is within the knowledge of the art to select and combine biomass types for use in the present invention. For example, the biomass can comprise an energy crop alone, or municipal solid waste and yard waste, or forestry residue, paper waste and pulp waste, and on in any of the many possible combinations.

In accordance with the invention, biomass can be used with or without pretreatment before culturing with microorganisms to ferment the sugars in the mash and generate biofuel. Pretreatment can be done by physical (e.g., grinding), chemical (e.g., acid treatment) or biological (e.g., enzymatic hydrolysis) techniques, and methods therefor are well known in the art [see, e.g., Zheng et al. (2009) Int. J. Agric. & Biol. Eng. 2:51-67]. As used herein, unless the context shows otherwise, "biomass" includes such pretreated biomass.

The general aspects of culturing biomass with microorganisms as well as the equipment and apparatus needed are known to the ordinarily skilled artisan or can be readily determined, whether on the laboratory scale or on an industrial scale. See, Mielenz (2009) for an example of an industrial scale production system. Such general aspects include preparation of the biomass, introduction of the biomass and any other media into a fermentation reactor or vessel using sterile techniques, maintaining cultures and stocks of the microorganisms, timing of inoculation, amounts of an inoculum, the form of the inoculum (e.g., from exponentially growing cultures or from lag-phase cultures and otherwise), co-culturing of microorganisms in the fermentation, time length of the fermentation, appropriate thermophilic growth conditions, removal or purification of the biofuel from the fermentation mixture or mash and more.

The fermentative conversion processes that breakdown biomass to produce biofuel include, but are not limited, to separate hydrolysis and fermentation (SHF); simultaneous cellulose hydrolysis (or saccharification) and fermentation (SSF); simultaneous saccharification and cofermentation (SSCF); and consolidated bioprocessing (CBP). Each of these processes can be practiced with the proteins or anaerobic, thermophilic microorganisms of the invention at any stage thereof. The preferred growth format is CBP. While the ability to conduct CBP has not yet been achieved with a single, aldehyde-tolerant, anaerobic, thermophilic microorganism (capable of cellulose and hemicellulose hydrolysis as well as hexose and pentose sugar fermentation), the present invention provides a way to achieve aldehyde tolerance.

The duration needed for fermentation that yields high substrate conversion lasts for the time needed to produce biofuel and can be determined by those of skill in the art. For example, fermentation to end products should occur in the shortest time possible to allow maximum and efficient conversions of the biomass before exhaustion of the substrate. An example of good substrate conversion would be to achieve at least about 50%, 55%, 60%, 65%, 70% or 75% conversion over a time period of from at least about 30 to about 200 hours or from at least about 50 to about 150 hours.

A still additional aspect of the invention provides methods to produce bulk and platform chemicals, including alcohols, by (a) removing sufficient inhibitory aldehydes in a lignocellulosic mixture undergoing a fermentative reaction to produce bulk or platform chemicals by adding one or more polypeptides of the invention to said mixture in an amount and for a time sufficient to convert such aldehydes to nontoxic compounds, and (b) recovering the bulk or platform chemical of interest. Examples of bulk and platform chemicals include ethanol, butanol, lactate, 1,4-dicarboxylic acids (succinic, fumaric, malic), glycerol, sorbitol, mannitol, arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, 3-hydroxybutyrolactone, fatty acids, fatty-derived molecules, isoprenoids, isoprenoid-derived molecules, alkanes, isopentanol, and isoamylacetate. When using the polypeptides of the invention, increased specific productivity (gram product per gram cell and hour) can be achieved due to the faster removal of inhibitory furan compounds and carbonyl compounds from the medium.

A further aspect of the invention relates to methods to produce butanol from biomass which comprises culturing biomass with an anaerobic, thermophilic microorganism of the invention for a time and under fermentation conditions suitable to produce butanol and recovering the butanol. The invention also contemplates similar methods for producing ethanol, furfuryl alcohol, and/or 2,5-(dihydroxymethyl) furan, by culturing as for butanol production and recovering the desired alcohol. Depending on the source of biomass, certain alcohols may predominate over others, for example, using the method with furan waste from pulp or paper processing is advantageous for recovering furfuryl alcohol. These methods are practiced as described above for biomass conversion to biofuel.

Methods for recovery and downstream processing of biofuel, specific alcohols and bulk and platform chemicals are known in the art. For example, ethanol can be recovered by distillation, and using a thermophilic process is an advantage in that regard, especially when working on an industrial scale. Ethanol can be removed from fermentation reactors as it is produced to avoid its toxic effects on microorganisms and methods for such removal are known in the art. Butanol can be recovered by adsorption techniques. All the methods of the invention can be practiced on any scale, from small batches in a laboratory to industrial scale production.

The foregoing is considered as illustrative of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All referenced patents, patent applications or other documents cited are herein incorporated by reference in their entirety.

EXAMPLE 1

Identification of a Teth39E Fe-Dependent, Alcohol Dehydrogenase

The saccharolytic thermophile *Thermoanaerobacter pseudethanolicus* 39E (Teth39E) tolerates furfural and HMF, and reduces these compounds to their respective alcohols.

Teth39E (DSMZ 2355) was purchased from Deutsche Sammlung von Mikroorganismen and Zellkulturen GmbH (DSMZ). Anaerobic growth medium was prepared anaerobically by a modified Hungate technique and consisted of 4.5 mM KCl, 4.7 mM NH4Cl, 2.5 mM MgSO4.7H2O, 1.0 mM NaCl, 0.7 mM CaCl2.2H2O, 0.25 mg/ml resazurin, 2.8 mM cysteine-HCl, 6.0 mM NaHCO3, 1 mM potassium phosphate buffer (pH 6.8), 10 mM 3-(N-morpholino)-propanesulfonic acid (pH 6.8), 1× Wolfe's trace minerals, 1× Wolfe's vitamin supplement, 0.1% (w/v) yeast extract, and 40 mM glucose [Miller and Wolin (1974) *Appl. Microbiol.* 27:985-987; Wolin et al. (1963) *J. Biol. Chem.* 238:2882-2886]. Furan aldehydes were added from degassed concentrated stock solutions. Cultures were grown at 65° C. from a 1% inoculum in Balch tubes (10 mL) or 125 mL serum bottles (50 mL) Cell growth was monitored by optical density at 600 nm, either directly in the Balch tube using a Spectronic 200 spectrophotometer (Thermo Fisher Scientific, Waltham, Mass.) or as 200 µL samples transferred to a 96-well plate and read on a Synergy Mx plate reader (BioTek, Winooski, Vt.). All growth experiments were performed in triplicate.

Figure 1A:
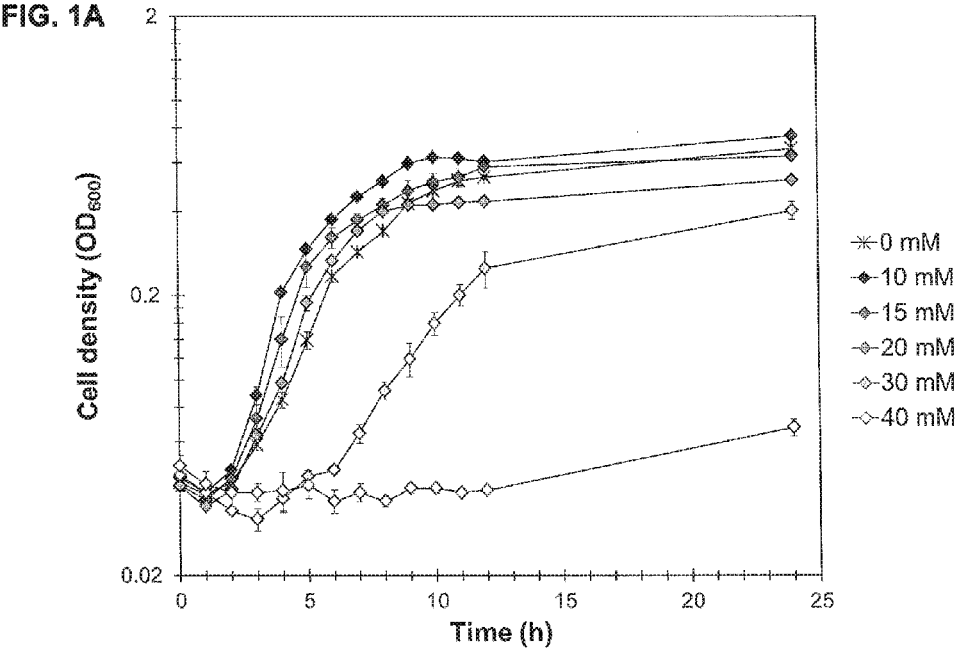
FIG. 1A depicts a line graph showing the growth of Teth39E with increasing concentrations of furfural as measured by optical density at 600 nm.
Figure 1B:
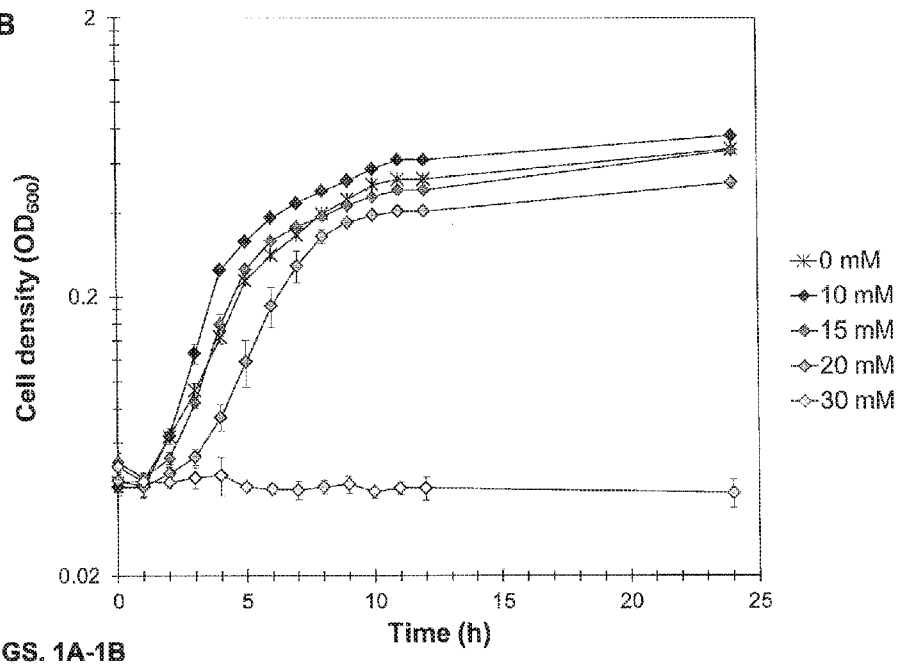
FIG. 1B shows a line graph of growth of Teth39E with increasing concentrations of 5-HMF.

Lower concentrations of furfural (10 and 20 mM) and 5-hydroxymethylfurfural (10 mM) stimulated growth of Teth39E, with increased cell yields after 12 h for both (see FIGS. 1A and 1B). Furfural addition increased specific growth rate at both 10 mM (0.52±0.03 h$^{-1}$) and 20 mM (0.43±0.03 h$^{-1}$) versus the control without furfural (0.38±0.01 h$^{-1}$) (see FIG. 1A) and 5-hydroxymethylfurfural (5-HMF) also increased specific growth rate at 10 mM versus the control (0.51±0.03 v. 0.41±0.02 h$^{-1}$) (see FIG. 1B). The furan aldehyde concentration which resulted in 50% inhibition of growth ($IC_{50}$) with furfural was 30 mM after 12 h and 30 to 40 mM after 24 h. The $IC_{50}$ for 5-HMF was between 20 and 30 mM after both 12 and 24 h.

Figure 2A:
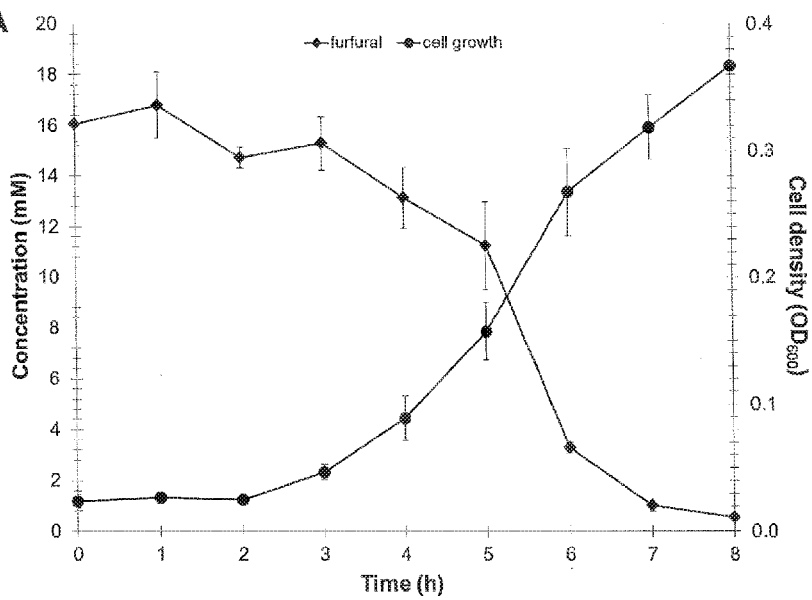
FIG. 2A presents the furfural concentration in medium during growth of Teth39E.
Figure 2B:
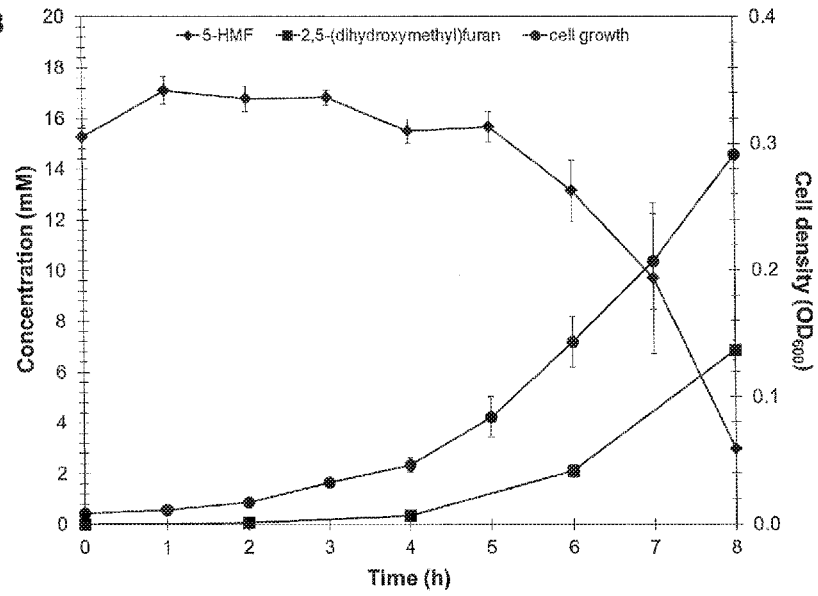
FIG. 2B shows 5-HMF and 2,5-(dihydroxymethyl)furan concentrations in medium during growth of Teth39E. Furan aldehyde concentration was measured spectrophotometrically, while furan alcohol concentration was measured by GC-MS.
Figure 3:
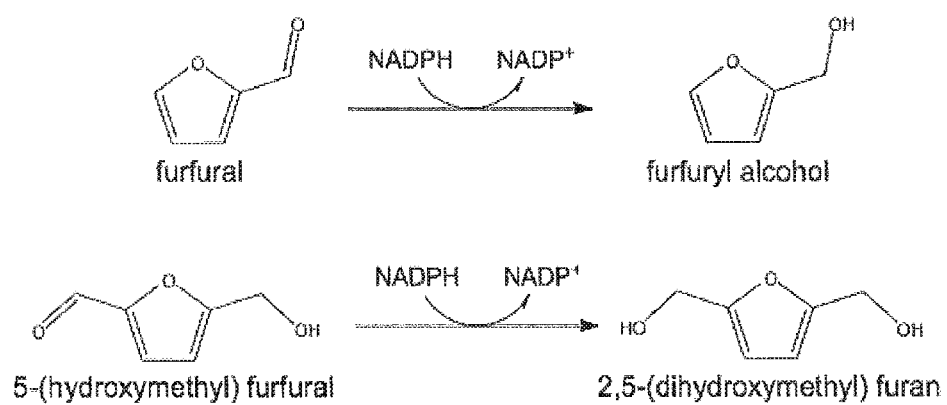
FIG. 3 shows a line drawing of the reduction of furfural and 5-HMF to their respective alcohols, furfuryl alcohol and 2,5-(dihydroxymethyl)furan, using NADPH.

Furfural and 5-HMF were measured spectrophotometrically (DU 800, Beckman Coulter, Brea, Calif.) at 304 and 323 nm, respectively, and concentrations were determined using standard curves generated in growth medium. In addition, 2,5-(dihydroxymethyl)furan was measured using GC-MS. Teth39E was grown in the presence of 15 mM furfural or 5-HMF and furan aldehyde and respective furan alcohol concentrations were measured along with growth, either spectrophotometrically or by GC-MS. As shown in FIGS. 2A and 2B, furfural (FIG. 2A) and 5-HMF (FIG. 2B) concentration decreased and 2,5-(dihydroxymethyl)furan concentration increased concomitant with growth, indicating reduction of 5-HMF by Teth39E. Furfural was most likely also reduced to furfuryl alcohol; however, detection of the latter is complicated by its polymerization at the growth temperature of Teth39E.

The gene product of Teth39_1597 is an aldehyde reductase (BdhA) that reduces furfural and 5-HMF to furfuryl alcohol and 2,5-(dihydroxymethyl)furan in an NADPH-dependent manner. See FIG. 3.

EXAMPLE 2

Characterization of BdhA

To identify the enzymes responsible for furfural and 5-HMF conversion, the proteomes were compared for strain Teth39E grown in the presence or absence of 15 mM furfural. Many proteins were upregulated at least 2-fold by furfural, including homologs of proteins involved in furfural detoxification in *Escherichia coli* (Miller 2009), and these proteins were targeted for further investigation. The protein encoded by the Teth39_1597 locus is a predicted Fe-dependent, alcohol dehydrogenase (bdhA) and the expression was upregulated approximately 7-fold in the presence of 15 mM furfural.

The bdhA gene was PCR amplified from Teth39E genomic DNA and cloned into *E. coli* expression vector pET30a (see FIG. 6A) under control of an IPTG-inducible, strong T7 promoter via the methods described below.

Teth39E genomic DNA was isolated using the Wizard Genomic DNA Purification kit (Promega, Madison, Wis.). The bdha gene was PCR amplified using Phusion polymerase (New England Biolabs, Ipswich, Mass.) and cloned into pET30a (EMD Millipore, Billerica, Mass.) behind 6× His- and S-tags. See FIG. 6A. Expression plasmids were transformed in BL21 (DE3) *E. coli* according to the manufacturer's protocol (Invitrogen, Grand Island, N.Y.). Cells were grown in 50 mL 2×YT medium at 37° C. to $OD_{600}$ of 0.8-1.0, then induced with 100 µM isopropyl-β-D-thiogalactopyranoside and switched to 30° C. for 16 h. Cells were harvested at 4° C. (3,000×g, 30 min), washed in 50 mL 100 mM sodium phosphate buffer, pH 7 (buffer A), and resuspended in 5 mL buffer A. Enzyme assays were performed aerobically at 60° C. with whole cell lysates and specific activity was determined by measuring the change in absorbance at 340 nm due to oxidation of NADPH or NADH.

Cell suspension (450 µL) was added to 0.1 mm zirconia beads (300 µL) and vortexed 4×60 sec with 30 sec on ice in between. Samples were centrifuged (14,000×g, 2 min) and the resulting supernatant was used for enzyme assays.

For the enzyme assays, Buffer A (1 mL), 10 mM NAD(P)H (25 µL), and 400 mM aldehyde (50 µL) were added to a 2 mL quartz cuvette, sealed with a butyl stopper, and equilibrated to 60° C. Assays were read at 340 nm (DU 800) for 150 sec to establish a baseline slope before whole cell lysate was added (1-5 µL). Cuvettes were inverted once to mix and read an additional 450 sec. The decrease in absorbance over time was calculated and the baseline slope was subtracted. NAD(P)H concentration was determined using the extinction coefficient (NADH: 6220 $M^{-1}$ $cm^{-1}$, NADPH: 6270 $M^{-1}$ $cm^{-1}$) and specific activity was calculated as the change in µmoles NAD(P)H/min/mg of whole cell lysate protein. Protein concentration was determined using the Bradford assay (Bio-Rad, Hercules, Calif.) with bovine serum albumin as a standard. Specific activity was measured for the pET30a vector (control) and overexpressed Teth39_1597 (BdhA) with acetaldehyde, butyraldehyde, isobutyraldhyde, furfural, and 5-HMF. Furfural was also assayed under anaerobic conditions. BdhA activity was compared to the vector-only control.

Figure 7:
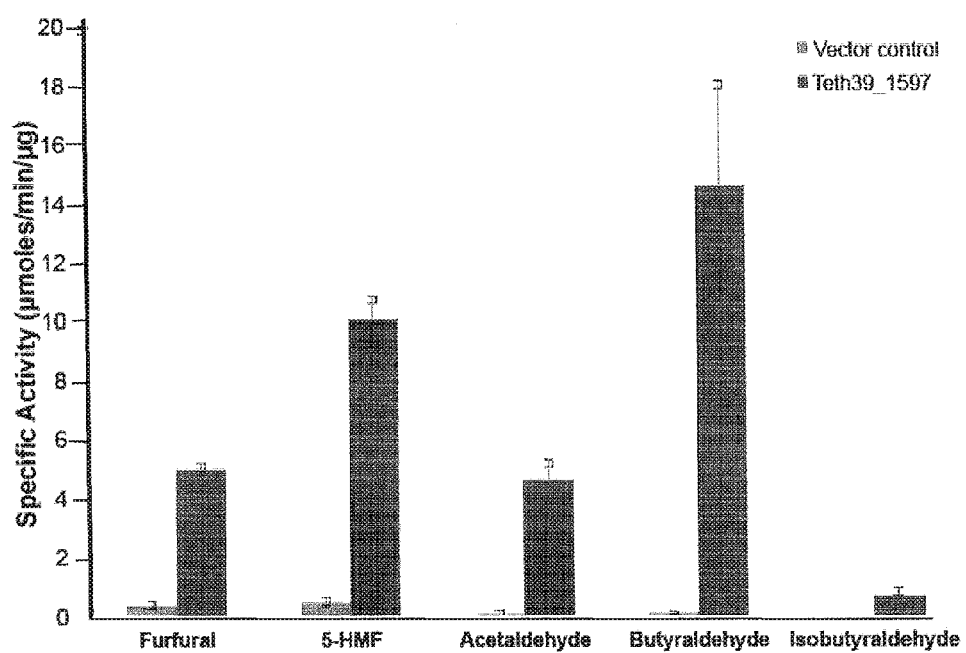
FIG. 7 depicts a bar graph showing the aldehyde reductase activity in the presence of NADPH of cell lysates containing pET-30a-Teth39_1597 or a control plasmid. The aldehydes, from left to right, are furfural, 5-HMF, acetaldehyde, butyraldehyde and isobutyraldehyde.

BdhA showed activity above the vector control under aerobic conditions using NADPH as cofactor with both furan aldehydes. The assays showed reducing activity for furfural, 5-HMF, butyraldehyde, isobutyraldehyde, and acetaldehyde in the presence of NADPH (see Table 1 and FIG. 7). Specific activity was 4.97±0.17 U with furfural and 10.06±0.80 U with 5-HMF. The highest activity was observed against butyraldehyde (approximately 14.58±3.57 µmoles/min/mg) while the lowest activity occurred with isobutyraldehyde as the substrate. No activity was detected with BdhA (above the vector control) using NADH as the cofactor, and no other cofactors were required.

TABLE 1

| BdhA Aldehyde Activities | | |
|---|---|---|
| Substrate | Vector control | BdhA |
| Furfural | 0.33 ± 0.13 | 4.97 ± 0.17 |
| 5-HMF | 0.44 ± 0.16 | 10.06 ± 0.80 |
| Acetaldehyde | 0.02 ± 0.15 | 4.54 ± 0.76 |
| Butyraldehyde | 0.09 ± 0.05 | 14.58 ± 3.57 |
| Isobutyraldehyde | −0.10 ± 0.21 | 0.63 ± 0.29 |

When overexpressed in *E. coli*, the Teth39E expression BdhA vector produced a protein of the correct molecular weight whereas the control vector did not as shown by SDS PAGE and Coomassie blue staining (see FIG. 6B). The overexpressed protein had an expected molecular weight of 48 kD, including N-terminal tags and cleavage sites.

Figure 8:
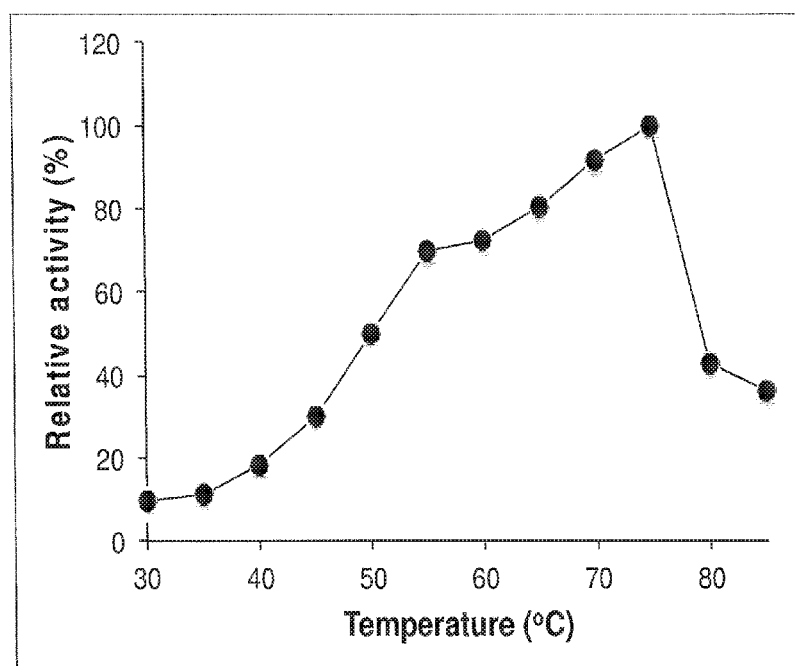
FIG. 8 shows a line graph of BdhA relative activity at temperatures ranging from 30 to 85° C.

The optimal temperature for BdhA activity was determined from purified enzyme as follows. A 1 liter culture of *E. coli* BL21 (DE3) harboring the pET30a-BdhA expression construct (see FIG. 6A) was grown to mid-log phase and induced with 0.4 mM IPTG and allowed to incubate for 16 h at 30° C. with shaking at 250 rpm. The induced cells were harvested via centrifugation at 5,000×g for 20 min at 4° C. and washed 3 times with 40 mL ice-cold phosphate buffered saline (PBS) at pH 7.2 and placed on ice. The cell pellet was resuspended in binding buffer (20 mM sodium phosphate, 500 mM NaCl, 20-40 mM imidazole, pH 7.4) containing 0.2 mg/mL lysozyme, 20 µg/mL DNAse, 1 mM $MgCl_2$, 1 mM PMSF and stirred for 30 min at room temperature. The cells were then subjected to 5×2 min rounds of sonication (Branson Sonifier 450 with microtip, duty cycle at 30%) while kept in an ice water bath. The lysate was centrifuged at 7,500×g for 20 min at 4° C. and the supernatant was transferred to a new 50 mL conical tube. Purification of the 6× His tagged BdhA enzyme was performed using 1 mL HisTrap FF crude affinity column according to the supplier's protocol (GE Healthcare, Piscataway, N.J., USA). Enzyme assays were performed as described above only 3 µg of purified BdhA enzyme was used rather than crude lysate. For determining the optimal temperature for BdhA, 1 mL assays containing 100 mM phosphate buffer (pH 7.5), 20 mM butyraldehyde, and 0.25 mM NADPH were monitored for loss of absorbance at 340 nm for 20 seconds at 30-90° C. in 5° C. intervals. Each assay was preheated to the appropriate temperature before adding 3 µg of purified BdhA enzyme. A temperature controlled cuvette holder (Shimadzu UV-800) was used to maintain assay temperature. The results are shown in FIG. 8. The optimal temperature was observed to be 75° C.

Figure 9:
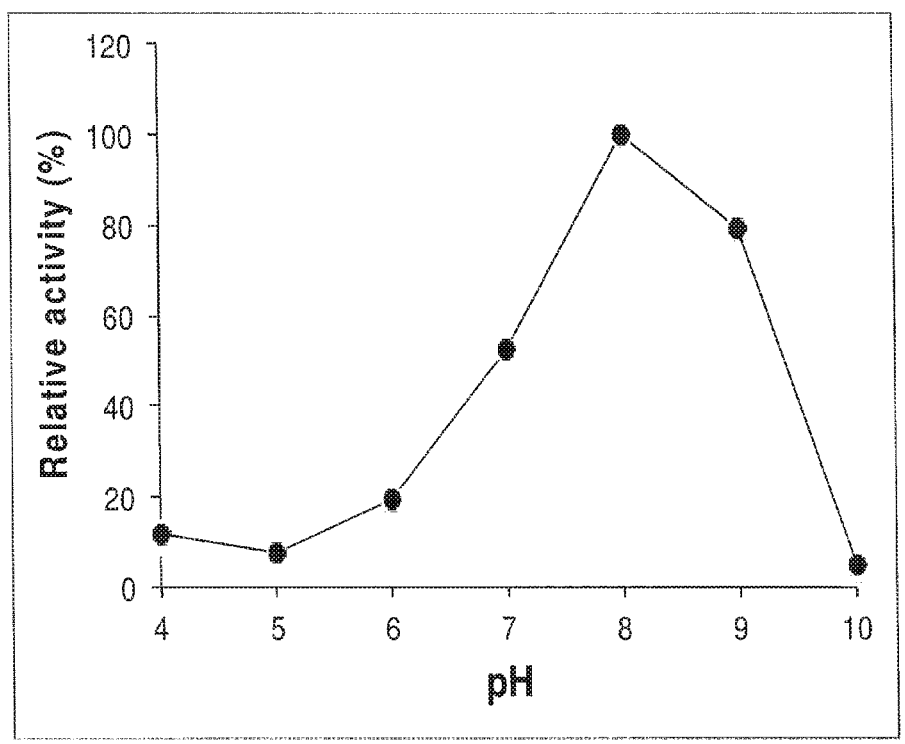
FIG. 9 presents a line graph of BdhA relative activity at pH 4 to 10.

The optimum pH was also determined for BdhA by using butyraldehyde as the substrate and NADPH as the cofactor. The assay conditions were as described above but a series of buffers increasing in pH from 4-10 were substituted for 100 mM phosphate buffer (pH 7.5). The optimal relative activity was found to be at a value of 8.0 pH units. See FIG. 9.

Figure 10A:
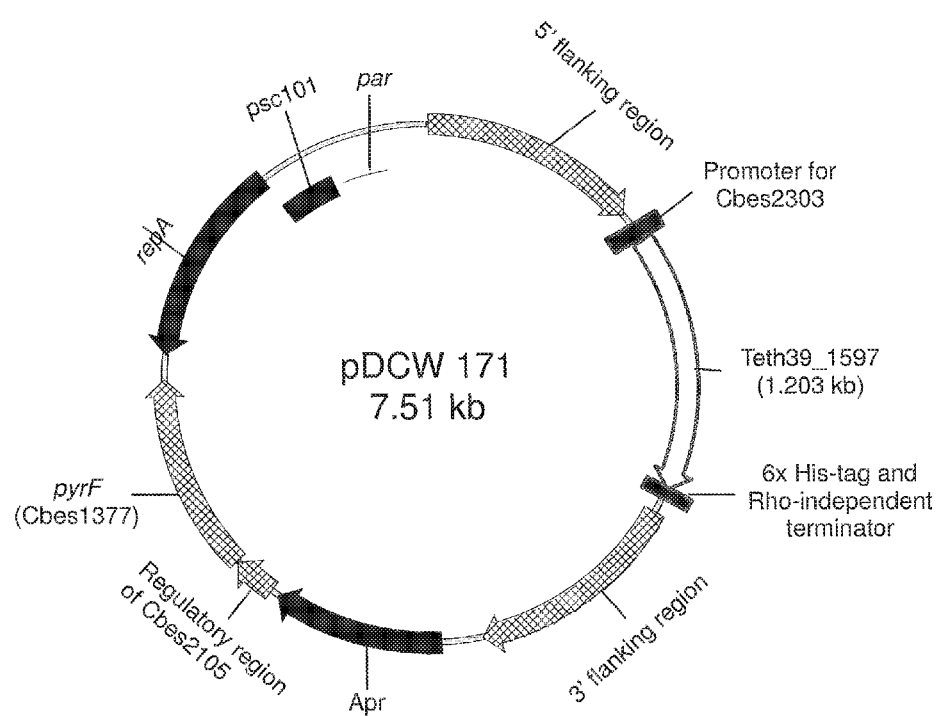
FIG. 10A presents a schematic diagram of the pDCW 171 Teth39_1597 expression cassette integration vector. Key: Ap$^r$, apramycin resistant gene cassette; pSC101, low copy replication origin in *E. coli;* repA, a plasmid-encoded gene required for pSC101 replication; par, partition locus.
Figure 10B:
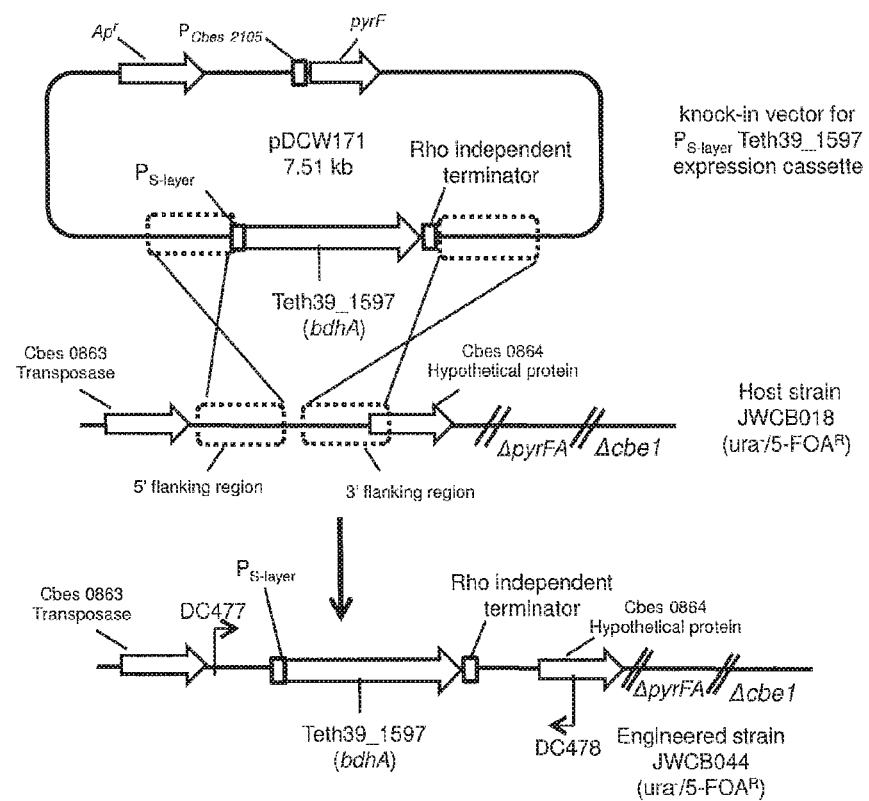
FIG. 10B shows a graphical representation of the mechanism by which the pDCW 171 Teth39_1597 expression cassette integration vector integrates the bdhA gene into a host cell genome.

The bdhA gene was inserted into the genome of the cellulolytic, thermophilic microorganism, *Caldicellulo-* siruptor bescii. The coding sequence for BdhA the bdhA gene set forth in SEQ ID NO: 1 was PCR amplified from *Thermoanaerobacter pseudethanolicus* 39E and cloned into the shuttle vector pDCW 171 (FIG. 10A), generating the BdhA expression cassette, which consists of the bdha coding region flanked by a strong promoter (P$_{s\text{-}layer}$) at the 5' end and a 6× His-tag plus Rho-independent terminator at the 3' end. Flanking the expression cassette are two kb sequences enabling homologous recombination into a targeted area in the chromosome. Also included in the pDCW 171 vector is a pyrF cassette allowing for uracil prototrophic selection of transformants. The construct was transformed into a *C. bescii* host strain (JWCB018) according to the methods described in Chung et al. [PNAS, 2014, 111:8931-8936]. Homologous recombination can occur at either the upstream or the downstream targeted chromosomal region, integrating the plasmid into the genome and generating a strain that is a uracil prototroph due to integration of the pyrF cassette on pDCW 171. Counter-selection with 5-fluoroorotic acid (5-FOA) selects for loss of the plasmid sequences, specifically the pyrF cassette, but not the BdhA expression cassette. Bent arrows depict primers used for verification of the integrated expression cassette (see FIG. 10B).

```
                                            SEQ ID NO: 1
atgATGAAAT TTGAATTTTA TAACCCGACC CGACTAATTT

TTGGTGCAGG TTCATTAGGA CAGTTAGGTA AAGTAGTTAA

TCAATATGGT AAAAAAGCAT TGCTTGTCAT TGGTGGTGGA

AGTGTAAAGA AAAGTGGAGC GTTTGATCGA GCAGTAGCAA

GTCTCAAAGC AGCGGGTGTT TTAGTGGTAG AATTCTCAGG

TGTTGAGCCA AACCCCCGCC TGTCAACTGT AGTGCGTGCT

TCAGAACTGG CAAAAAAGA AGCATGTGAT GTGGTTATAG

GTATGGGTGG CGGTAGCGTC ATGGACGCCT CAAAAGTAAT

TGCAGCCTCA GTCCTTTATG AAGGCGATCC TAAGGATATG

CTTGTACGGG CAGGAAAAGC GCCCAGGCTG CCGGAGCGAG

CTCTTCCTAT TATCACTGTT CCTACCCTGG CGGCAACTGG

CTCGGAAATG AACAACGGTG CGGTGATCAC GATTGACGAT

GAAGGAGAAA AGCTAAAAAC ATTCGTTCAG GCCGAGGTTC

TCTATCCTCG AGTGGCAGTG GTGGATCCTG AACTTACGAT

GACAGTGCCC AAGAATCACA CAGCTTTTGG GGTTTGCGAT

ATAATAACCC ATGTGACCGA GGGTTATTTT AACGGTATAG

ACGGGACTCC TCTTCAGGAC AGATTTGCCG AGGGAGTGAT

CCTTACTGTC TTGGAGTGGG GACCAAAGGC GGTTAGTGAT

GGAAGTGACC TGGAAGCGCG CACTCAGGTG CAGTGGGCGT

CGATAGTTGC TCTTAATGGG TGGGTACAAG TAGGAACAAA

CGGAGCGTAC CCTGTTCATA TGATCGAGCA CACACTTTCC

GCACTCTACG ATATCCCCCA TGGAGCAGGG TTAGCAGTCG

TGAACCCCGC TTGGATGCGC TTTGCTGCAA GATTCCGCCC

CGAACGTTTT GCCCAATTTG CTCAACGTAT CTTTGGTTTG

ACAGCAACAG GCAAAGACAC CTTGAGCCTT GCCATGGAAG
```

```
                                            -continued
GTATTGATAA GTTTGAAGAG TTCTTGCGTT CAATAGGTTG

TCCTACACGC TTGTCGGAAT TGGGCATTGG AGAAATTACC

GAGGAAATGC TTTTCCGTTA TGCGGAAGAG ACGCTGAAAG

TGCTTCAGGA TGAAGAAGGA AGGCTTCCAG GTCGTCCCTC

TCTGCGAAAG GAAGATATTG TAGAAATACT ACGCATGGCA ATGtga

SEQ ID NO: 2
MMKFEFYNPT RLIFGAGSLG QLGKVVNQYG KKALLVIGGG

SVKKSGAFDR AVASLKAAGV LVVEFSGVEP NPRLSTVVRA

SELAKKEACD VVTGMGGGSV MDASKVIAAS VLYEGDPKDM

LVRAGKAPRL PERALPIITV PTLAATGSEM NNGAVTTIDD

EGEKLKTFVQ AEVLYPRVAV VDPELTMTVP KNHTAFGVCD

IITHVTEGYF NGIDGTPLQD RFAEGVTLTV LEWGPKAVSD

GSDLEARTQV QWASIVALNG WVQVGTNGAY PVHMTEHTLS

ALYDIPHGAG LAVVNPAWMR FAARFRPERF AQFAQRIFGL

TATGKDTLSL AMEGIDKFEE FLRSIGCPTR LSELGIGEIT

EEMLFRYAEE TLKVLQDEEG RLPGRPSLRK EDIVEILRMA M.
```

Figures 11A, 11B, 11C:
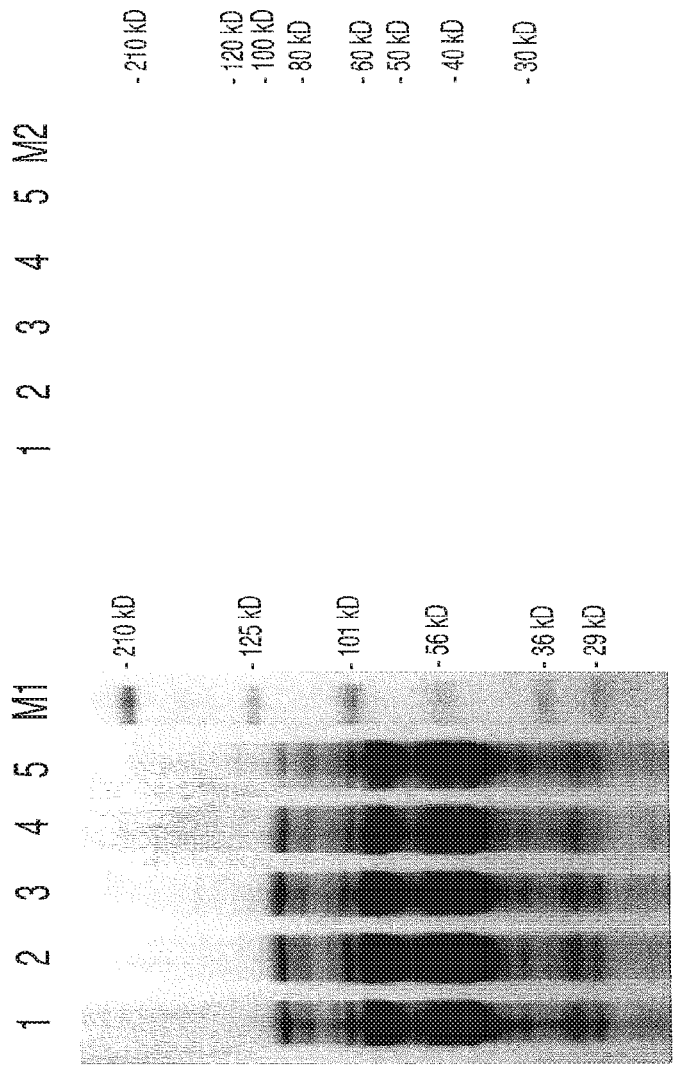
FIG. 11A-11C shows the expression of *T. pseudethanolicus* bdhA in *C. bescii*.

Transformants were selected on a minimal medium without uracil. Counter-selection for double recombinants and loss of the suicide plasmid were screened for by picking colonies onto media containing 5-FOA. PCR was used to verify integration of the bdhA gene allele at the target locus within the chromosome (FIG. 11A). The total cellular protein was separated on an SDS-PAGE gel for wild-type *C. bescii;* the parent strain (JWCB018), and the expression strain JWCB044 grown at 65, 70, and 75° C. (FIG. 11B). The separated proteins were stained with Coomassie blue, transferred to a blotting membrane and subjected to Western analysis using anti-His antibodies (FIG. 11B). The BdhA enzyme was heterologously expressed in *C. bescii* at 65-75° C. as indicated by antibody detection in total cell protein.

Figure 12:
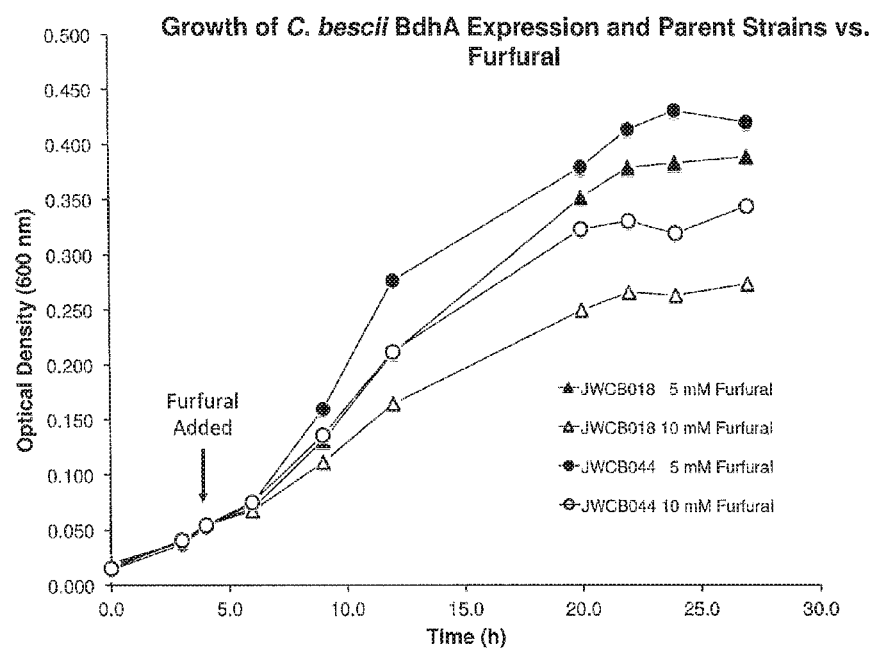
FIG. 12 depicts a line graph showing growth of *C. bescii* strains JWCB018 (lacking BdhA expression), and JWCB044 (expressing BdhA), in the presence of 5 and 10 mM furfural.
Figure 13:
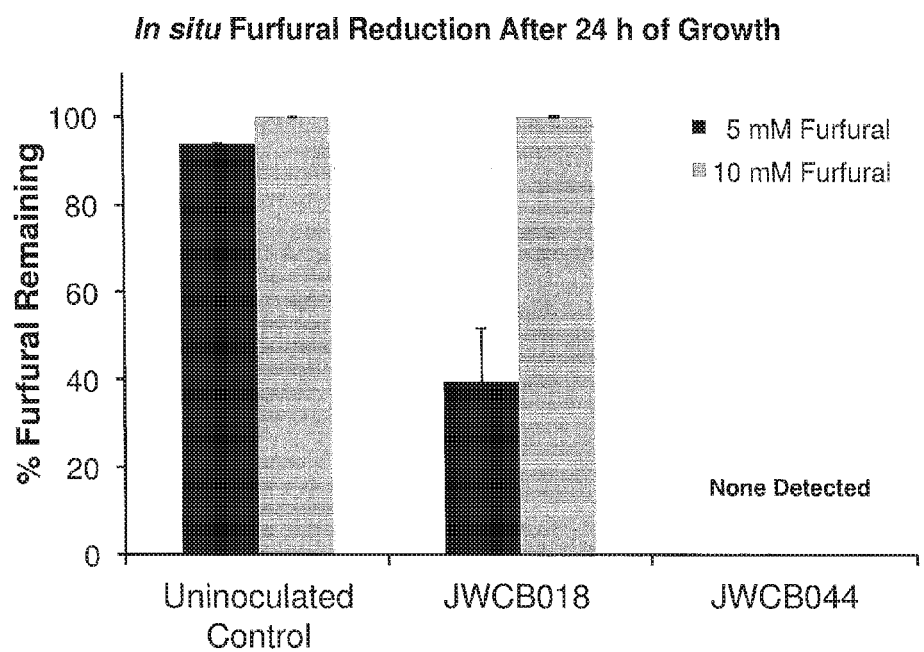
FIG. 13 shows a bar graph presenting relative remaining furfural concentrations after 24 h incubation of medium only with 5 and 10 mM furfural (uninoculated control), *C. bescii* strain JWCB018 (lacking BdhA expression), and *C. bescii* strain JWCB044 (expressing BdhA).

Growth experiments were conducted to test the phenotype of a *C. bescii* strain expressing BdhA (JWCB044) compared to a parent strain (JWCB018) when exposed to 5 and 10 mM furfural. The cells were grown in 10 mL of a minimal defined medium [Farkas et al. (2013) J. Ind. Microbiol. Biotechnol. 40:41-49] in Balch tubes incubated at 75° C. with shaking at 100 rpm. Experiments were inoculated in triplicate at equal cell densities from fresh overnight cultures. Growth was measured by placing individual Balch tubes in a Spec20 spectrophotometer and recording the absorbance at 600 nm. Furfural was added after 4 h of incubation and growth was measured periodically for 28 h. Compared to the parent strain control (JWCB018), the BdhA expression strain (JWCB044) displayed increased cell densities at 24 h of growth by 12.2% for the 5 mM furfural treatment and 21.7% when 10 mM furfural was added. See FIG. 12. A 15 mM furfural treatment, when applied to both JWCB018 and JWCB044 resulted in an improvement in the final OD600 values by 49% in JWCB044 after 24 h of growth. The residual furfural concentration was measured via HPLC analysis in cultures of JWCB018 and JWCB044 after 24 h of growth in the presence of either 5, 10, or 15 mM furfural. Uninoculated controls showed no degradation of furfural over time. When exposed to 5 mM furfural, the parent strain displayed some ability to reduce furfural to furfuryl alcohol in situ; however, at 10 mM furfural, no furfural was reduced and 100% remained in the medium after 24 h. In contrast, the strain expressing BdhA showed a dramatic difference in furfural concentration, with no detectable furfural remaining in any culture after 24 h. See FIG. 13. These results demonstrate that the engineered strain expressing BdhA is improved over the parent strain (which is derived from the wild-type) and tolerates significant concentrations of the furan aldehyde, furfural.

EXAMPLE 3

Bacterial Homology to BdhA

Table 2 lists the sequenced microorganisms that have coding sequences that share at least 60% identity and homology with BdhA as determined by the BLAST algorithm in May 2013.

TABLE 2

| Strain | % identity | Protein Accession No. |
| --- | --- | --- |
| *Thermoanaerobacter pseudethanolicus* ATCC 33223 | 100% | YP_001665577.1 |
| *Thermoanaerobacter brockii* subsp. *finnii* Ako-1 | | |
| *Carboxydothermus hydrogenoformans* Z-2901 | 96% | YP_360528.1 |
| *Thermacetogenium phaeum* DSM 12270 | 92% | YP_006920865.1 |
| *Syntrophothermus lipocalidus* DSM 12680 | 93% | YP_003701586.1 |

TABLE 2-continued

| Strain | % identity | Protein Accession No. |
| --- | --- | --- |
| *Thermoanaerobacter mathranii* subsp. *mathranii* str. A3 | 89% | YP_003677126.1 |
| *Thermoanaerobacter mathranii* | 89% | CAZ39598.1 |
| *Thermoanaerobacter italicus* Ab9 | 89% | YP_003476555.1 |
| *Thermococcus litoralis* DSM 5473 | 70% | ZP_09730910.1 |
| *Spirochaeta thermophila* DSM 6192 | 71% | YP_003874393.1 |
| *Chlorobium chlorochromatii* CaD3 | 69% | YP_380004.1 |
| *Desulfobulbus propionicus* DSM 2032 | 68% | YP_004194670.1 |
| *Geobacter bemidjiensis* Bem | 67% | YP_002137602.1 |
| *Geobacter* sp. M21 | 67% | YP_003020662.1 |
| *Desulfovibrio magneticus* RS-1 | 65% | YP_002951509.1 |
| *Chlorobium limicola* DSM 245 | 66% | YP_001943939.1 |
| *Chlorobium phaeovibrioides* DSM 265 | 64% | YP_001130471.1 |
| uncultured bacterium | 64% | EKD39159.1 |
| *Desulfovibrio* sp. U5L | 65% | ZP_10078352.1 |
| *Desulfovibrio desulfuricans* ND132 | 62% | YP_005167244.1 |
| *Desulfovibrio salexigens* DSM 2638 | 62% | YP_002993144.1 |
| *Chlorobium luteolum* DSM 273 | 63% | YP_374851.1 |
| *Thermanaerovibrio acidaminovorans* DSM 6589 | 64% | YP_003318139.1 |
| *Thermanaerovibrio velox* DSM 12556 | 62% | ZP_09412593.1 |
| *Carboxydothermus hydrogenoformans* | 86% | AAG23613.1 |

Although the various aspects of the invention have been illustrated above by reference to examples and preferred embodiments, it will be appreciated that the scope of the invention is defined not by the foregoing description but by the following claims properly construed under principles of patent law.

We claim:

1. A fermentation process comprising:
   contacting biomass with an anaerobic, thermophilic microorganism for a time and under thermophilic, anaerobic conditions to detoxify inhibitory aldehydes present in the biomass, and to allow fermentation of the biomass and conversion of the biomass to biofuel, wherein said biofuel comprises ethanol; and
   recovering ethanol from said biofuel,
   wherein said thermophilic microorganism comprises a nucleic acid encoding a polypeptide having NAD(P)H-dependent alcohol dehydrogenase activity and comprising an amino acid sequence having at least 95% sequence identity to the amino acid sequence of SEQ ID NO: 2, and wherein said nucleic acid is operably linked to a heterologous promoter.

2. The process of claim 1, wherein said biomass has been pretreated by acid hydrolysis, hot water, or enzymatic hydrolysis.

3. A method of improving the yield and/or efficiency of lignocellulosic biomass conversion to biofuel, comprising:
   contacting lignocellulosic biomass with an anaerobic, thermophilic microorganism for a time and under thermophilic, anaerobic conditions sufficient to detoxify inhibitory aldehydes present in said biomass, and to produce improved yields or efficiency of biomass conversion to biofuel, relative to lignocellulosic biomass that has not been so contacted, wherein said biofuel comprises ethanol; and
   recovering ethanol from said biofuel,
   wherein said thermophilic microorganism comprises a nucleic acid encoding a polypeptide having NAD(P)H-dependent alcohol dehydrogenase activity and comprising an amino acid sequence having at least 95% sequence identity to the amino acid sequence of SEQ ID NO: 2, and wherein said nucleic acid is operably linked to a heterologous promoter.

4. The method of claim 3, wherein said lignocellulosic biomass has been pretreated by acid hydrolysis, hot water, or enzymatic hydrolysis.

5. A lignocellulosic biomass fermentation process comprising:
   contacting lignocellulosic biomass with a first anaerobic, thermophilic microorganism and a second anaerobic, thermophilic microorganism for a time and under thermophilic, anaerobic conditions to detoxify inhibitory aldehydes present in the biomass and to allow fermentation of the biomass to proceed and conversion of biomass to biofuel, wherein said biofuel comprises ethanol; and
   recovering ethanol from said biofuel,
   wherein said first anaerobic, thermophilic microorganism comprises a nucleic acid encoding a polypeptide having NAD(P)H-dependent alcohol dehydrogenase activity and comprising an amino acid sequence having at least 95% sequence identity to the amino acid sequence of SEQ ID NO: 2, and wherein said nucleic acid is operably linked to a heterologous promoter.

6. The method of claim 5, wherein said lignocellulosic biomass has been pretreated by acid hydrolysis, hot water, or enzymatic hydrolysis.

7. An improved method of producing a bulk or platform chemical from lignocellulosic biomass, the improvement comprising:
   contacting said lignocellulosic biomass with an anaerobic, thermophilic microorganism for a time and under conditions to reduce the aldehyde content associated with said lignocellulosic biomass and to improve production efficiency or yield of said bulk or platform chemical relative to lignocellulosic biomass that has not been so contacted, and
   recovering the bulk or platform chemical, wherein the bulk or platform chemical comprises ethanol,
   wherein said anaerobic, thermophilic microorganism comprises a nucleic acid encoding a polypeptide having NAD(P)H-dependent alcohol dehydrogenase activity and comprising an amino acid sequence having at least 95% sequence identity to the amino acid sequence of SEQ ID NO: 2, and wherein said nucleic acid is operably linked to a heterologous promoter.

8. The method of claim 7, wherein said lignocellulosic biomass has been pretreated by acid hydrolysis, hot water, or enzymatic hydrolysis.

9. The method of claim 7, wherein the bulk or platform chemical further comprises, lactate, furfuryl alcohol, 1,4-dicarboxylic acids, glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, 3-hydroxybutyrolactone, fatty acids, fatty-derived molecules, isoprenoids, isoprenoid-derived molecules, alkanes, isopentanol, or isoamylacetate.

10. The method of claim 7, wherein the lignocellulosic biomass is furan waste from pulp or paper processing.

11. The method of claim 7, wherein the bulk or platform chemical is ethanol.

12. The method of claim 7, wherein the microorganism is selected from the group consisting of *Thermoanaerobacter brockii*, *Thermoanaerobacter ethanolicus*, *Thermoanaero-* bacter pseudethanolicus, *Thermoanaerobacterium aotearoense, Thermoanaerobacterium saccharolyticum, Thermoanaerobacterium thermosaccharolyticum, Thermoanaerobacterium xylanolyticum, Clostridium thermocellum, Clostridium straminisolvens, Clostridium thermocopriae, Caldicellulosiruptor bescii, Caldicellulosiruptor saccharolyticus, Caldicellulosiruptor hydrothermalis, Caldicellulosiruptor kristjanssonii, Caldicellulosiruptor kronotskyensis, Caldicellulosiruptor lactoaceticus, Caldicellulosiruptor owensensi, Caldicellulosiruptor acetigenus,* and *Caldicellulosiruptor obsidiansis.*

* * * * *

SEQUENCE LISTING

<160> NUMBER OF SEQ ID NOS: 2

<210> SEQ ID NO 1
<211> LENGTH: 1206
<212> TYPE: DNA
<213> ORGANISM: Thermoanaerobacter pseudethanolicus

<400> SEQUENCE: 1

```
atgatgaaat ttgaatttta taacccgacc cgactaattt ttggtgcagg ttcattagga      60
cagttaggta aagtagttaa tcaatatggt aaaaaagcat tgcttgtcat tggtggtgga     120
agtgtaaaga aaagtggagc gtttgatcga gcagtagcaa gtctcaaagc agcgggtgtt     180
ttagtggtag aattctcagg tgttgagcca aaccccgcc tgtcaactgt agtgcgtgct      240
tcagaactgg caaaaaaga agcatgtgat gtggttatag gtatgggtgg cggtagcgtc     300
atggacgcct caaagtaat tgcagcctca gtcctttatg aaggcgatcc taaggatatg     360
cttgtacggg caggaaaagc gcccaggctg ccggagcgag ctcttcctat tatcactgtt     420
cctaccctgg cggcaactgg ctcggaaatg aacaacggtg cggtgatcac gattgacgat     480
gaaggagaaa agctaaaaac attcgttcag gccgaggttc tctatcctcg agtggcagtg     540
gtggatcctg aacttacgat gacagtgccc aagaatcaca cagcttttgg ggtttgcgat     600
ataataaccc atgtgaccga gggttatttt aacggtatag acgggactcc tcttcaggac     660
agatttgccg agggagtgat ccttactgtc ttggagtggg gaccaaaggc ggttagtgat     720
ggaagtgacc tggaagcgcg cactcaggtg cagtgggcgt cgatagttgc tcttaatggg     780
tgggtacaag taggaacaaa cggagcgtac cctgttcata tgatcgagca cacactttcc     840
gcactctacg atatccccca tggagcaggg ttagcagtcg tgaaccccgc ttggatgcgc     900
tttgctgcaa gattccgccc cgaacgtttt gcccaatttg ctcaacgtat ctttggtttg     960
```

-continued

```
acagcaacag gcaaagacac cttgagcctt gccatggaag gtattgataa gtttgaagag    1020
ttcttgcgtt caataggttg tcctacacgc ttgtcggaat tgggcattgg agaaattacc    1080
gaggaaatgc ttttccgtta tgcggaagag acgctgaaag tgcttcagga tgaagaagga    1140
aggcttccag gtcgtccctc tctgcgaaag gaagatattg tagaaatact acgcatggca    1200
atgtga                                                                1206
```

<210> SEQ ID NO 2
<211> LENGTH: 401
<212> TYPE: PRT
<213> ORGANISM: Thermoanaerobacter pseudethanolicus

<400> SEQUENCE: 2

```
Met Met Lys Phe Glu Phe Tyr Asn Pro Thr Arg Leu Ile Phe Gly Ala
1               5                   10                  15

Gly Ser Leu Gly Gln Leu Gly Lys Val Val Asn Gln Tyr Gly Lys Lys
            20                  25                  30

Ala Leu Leu Val Ile Gly Gly Ser Val Lys Lys Ser Gly Ala Phe
        35                  40                  45

Asp Arg Ala Val Ala Ser Leu Lys Ala Ala Gly Val Leu Val Val Glu
    50                  55                  60

Phe Ser Gly Val Glu Pro Asn Pro Arg Leu Ser Thr Val Val Arg Ala
65                  70                  75                  80

Ser Glu Leu Ala Lys Lys Glu Ala Cys Asp Val Val Ile Gly Met Gly
                85                  90                  95

Gly Gly Ser Val Met Asp Ala Ser Lys Val Ile Ala Ala Ser Val Leu
            100                 105                 110

Tyr Glu Gly Asp Pro Lys Asp Met Leu Val Arg Ala Gly Lys Ala Pro
        115                 120                 125

Arg Leu Pro Glu Arg Ala Leu Pro Ile Ile Thr Val Pro Thr Leu Ala
    130                 135                 140

Ala Thr Gly Ser Glu Met Asn Asn Gly Ala Val Ile Thr Ile Asp Asp
145                 150                 155                 160

Glu Gly Glu Lys Leu Lys Thr Phe Val Gln Ala Glu Val Leu Tyr Pro
                165                 170                 175

Arg Val Ala Val Val Asp Pro Glu Leu Thr Met Thr Val Pro Lys Asn
            180                 185                 190

His Thr Ala Phe Gly Val Cys Asp Ile Ile Thr His Val Thr Glu Gly
        195                 200                 205

Tyr Phe Asn Gly Ile Asp Gly Thr Pro Leu Gln Asp Arg Phe Ala Glu
    210                 215                 220

Gly Val Ile Leu Thr Val Leu Glu Trp Gly Pro Lys Ala Val Ser Asp
225                 230                 235                 240

Gly Ser Asp Leu Glu Ala Arg Thr Gln Val Gln Trp Ala Ser Ile Val
                245                 250                 255

Ala Leu Asn Gly Trp Val Gln Val Gly Thr Asn Gly Ala Tyr Pro Val
            260                 265                 270

His Met Ile Glu His Thr Leu Ser Ala Leu Tyr Asp Ile Pro His Gly
        275                 280                 285

Ala Gly Leu Ala Val Val Asn Pro Ala Trp Met Arg Phe Ala Ala Arg
    290                 295                 300

Phe Arg Pro Glu Arg Phe Ala Gln Phe Ala Gln Arg Ile Phe Gly Leu
305                 310                 315                 320
```

-continued

```
Thr Ala Thr Gly Lys Asp Thr Leu Ser Leu Ala Met Glu Gly Ile Asp
                325             330                 335

Lys Phe Glu Glu Phe Leu Arg Ser Ile Gly Cys Pro Thr Arg Leu Ser
            340             345                 350

Glu Leu Gly Ile Gly Glu Ile Thr Glu Glu Met Leu Phe Arg Tyr Ala
        355             360                 365

Glu Glu Thr Leu Lys Val Leu Gln Asp Glu Glu Gly Arg Leu Pro Gly
    370             375                 380

Arg Pro Ser Leu Arg Lys Glu Asp Ile Val Glu Ile Leu Arg Met Ala
385             390                 395                 400

Met
```